(12) United States Patent
Harada

(10) Patent No.: US 11,925,316 B2
(45) Date of Patent: Mar. 12, 2024

(54) ENDOSCOPE

(71) Applicant: FUJIFILM Corporation, Tokyo (JP)

(72) Inventor: Takashi Harada, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 877 days.

(21) Appl. No.: 16/826,300

(22) Filed: Mar. 23, 2020

(65) Prior Publication Data

US 2020/0214544 A1 Jul. 9, 2020

Related U.S. Application Data

(63) Continuation of application No. PCT/JP2018/035324, filed on Sep. 25, 2018.

(30) Foreign Application Priority Data

Sep. 27, 2017 (JP) ................. 2017-186561

(51) Int. Cl.
*A61B 1/00* (2006.01)
*A61B 1/012* (2006.01)
*A61B 1/018* (2006.01)

(52) U.S. Cl.
CPC ...... *A61B 1/00098* (2013.01); *A61B 1/00042* (2022.02); *A61B 1/00066* (2013.01);
(Continued)

(58) Field of Classification Search
CPC .............. A61B 1/00098; A61B 1/0008; A61B 1/00087; A61B 1/00101; A61B 1/00105;
(Continued)

(56) References Cited

U.S. PATENT DOCUMENTS 5,569,157 A * 10/1996 Nakazawa ......... A61B 1/00177
600/106
5,707,344 A 1/1998 Nakazawa et al.
(Continued)

FOREIGN PATENT DOCUMENTS

CN 102188220 9/2011
EP 1759626 5/2013
(Continued)

OTHER PUBLICATIONS

"Search Report of Europe Counterpart Application", dated Sep. 8, 2020, p. 1-p. 8.
(Continued)

*Primary Examiner* — Ryan N Henderson
*Assistant Examiner* — Pamela F Wu
(74) *Attorney, Agent, or Firm* — JCIPRNET

(57) ABSTRACT

Provided is an endoscope that can easily perform the attachment and detachment work of a proximal end side of a wire with respect to a slider.
An endoscope includes a base member (98) that forms a slider housing space (150) that is independent of an internal space of an operating part (22), an opening part (94) that is provided at a proximal end of a wire channel (62) and delivers the proximal end side of the wire (60) to a slider housing space (150), a slider (96) that is disposed in the slider housing space (150) and moves in a longitudinal direction of the operating part (22) depending on the operation of an erection operating lever (20) so as to be movable forward and backward, an engaged part (152) that is provided in the slider (96) and recessed toward a lateral side orthogonal to a movement direction of the slider (96), and an engaging member (154) that is provided at the proximal end of the wire (60) and is pushed into and engageable with the engaged part (152) from the lateral side.

8 Claims, 29 Drawing Sheets

(52) U.S. Cl.
CPC ...... *A61B 1/00105* (2013.01); *A61B 1/00137* (2013.01); *A61B 1/012* (2013.01); *A61B 1/018* (2013.01)

(58) Field of Classification Search
CPC .............. A61B 1/0011; A61B 1/00121; A61B 1/00066; A61B 1/00137; A61B 1/012; A61B 1/018; A61B 1/00174; A61B 1/00177; A61B 1/00179; A61B 1/273; A61B 1/005; A61B 1/0057; A61B 1/008; A61B 1/0052; A61B 1/00188; A61B 1/00039; A61B 1/00042; A61B 1/00112; A61B 1/00119; A61M 2025/0063
USPC .................................................. 600/106–107
See application file for complete search history.

(56) References Cited

U.S. PATENT DOCUMENTS

| | | |
|---|---|---|
| 7,846,090 B2 | 12/2010 | Pilvisto et al. |
| 2003/0073955 A1 | 4/2003 | Otawara |
| 2005/0209505 A1* | 9/2005 | Okada .................... A61B 1/018 600/106 |
| 2014/0094656 A1* | 4/2014 | Matsukawa ........ A61B 1/00114 600/110 |
| 2015/0148598 A1 | 5/2015 | Fukushima et al. |
| 2017/0065151 A1* | 3/2017 | Hatano ................ A61B 1/0051 |

FOREIGN PATENT DOCUMENTS

| | | |
|---|---|---|
| JP | S62227312 | 10/1987 |
| JP | H04005802 | 1/1992 |
| JP | H06315458 | 11/1994 |
| JP | H06315460 | 11/1994 |
| JP | H07194525 | 8/1995 |
| JP | 2002153420 | 5/2002 |
| JP | 2003305002 | 10/2003 |
| JP | 2004321697 | 11/2004 |
| JP | 3607743 | 1/2005 |
| JP | 2005205030 | 8/2005 |
| JP | 2015104424 | 6/2015 |
| JP | 2015107226 | 6/2015 |

OTHER PUBLICATIONS

"Office Action of China Counterpart Application" with English translation thereof, dated Nov. 3, 2021, p. 1-p. 17.
"Office Action of Japan Counterpart Application" with English translation thereof, dated Sep. 27, 2021, p. 1-p. 8.
Office Action of China Counterpart Application, with English translation thereof, dated May 20, 2022, pp. 1-15.
Office Action of Japan Counterpart Application, with English translation thereof, dated Apr. 5, 2021, pp. 1-8.
"International Search Report (Form PCT/ISA/210)" of PCT/JP2018/035324, dated Nov. 13, 2018, with English translation thereof, pp. 1-5.
"International Preliminary Report on Patentability (Form PCT/IPEA/409) of PCT/JP2018/035324", dated Oct. 8, 2019, with English translation thereof, pp. 1-7.
"Office Action of Japan Counterpart Application" with English translation thereof, dated Mar. 24, 2022, p. 1-p. 8.
"Office Action of Europe Counterpart Application", dated Feb. 1, 2023, pp. 1-4.

* cited by examiner

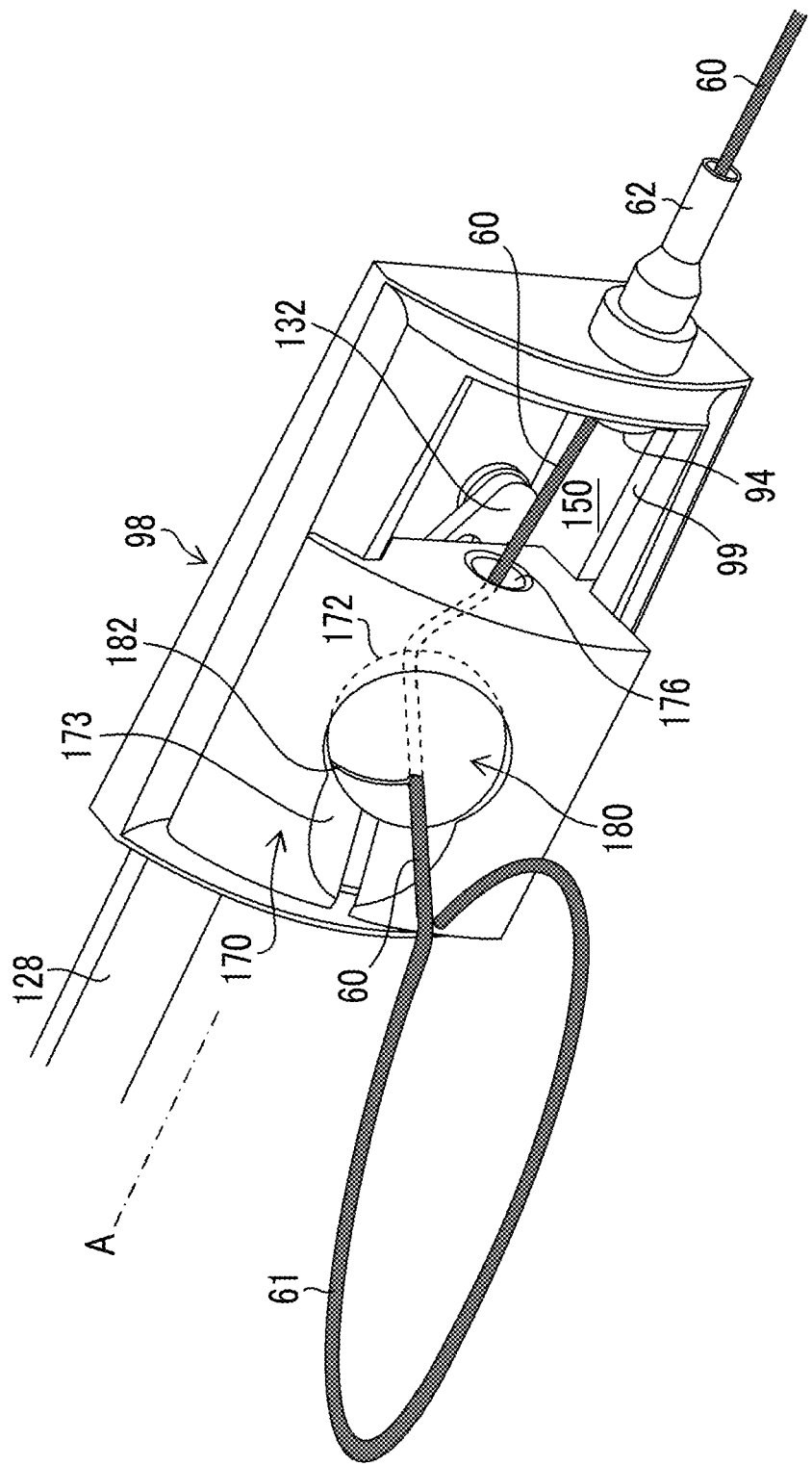

ENDOSCOPE

CROSS-REFERENCE TO RELATED APPLICATIONS

The present application is a Continuation of PCT International Application No. PCT/JP2018/035324 filed on Sep. 25, 2018 claiming priority under 35 U.S.C § 119(a) to Japanese Patent Application No. 2017-186561 filed on Sep. 27, 2017. Each of the above applications is hereby expressly incorporated by reference, in its entirety, into the present application.

BACKGROUND OF THE INVENTION

1. Field of the Invention

The present invention relates to an endoscope, and particularly, to an endoscope including a forceps elevator that changes a delivery direction of a treatment tool to a distal end part of an insertion part.

2. Description of the Related Art

In endoscopes, various treatment tools are introduced from a treatment tool introduction port provided in a proximal operating part (hereinafter referred to as an "operating part"), and the treatment tools are delivered from a treatment tool delivery port opening to a distal end member of an insertion part to the outside, and are used for treatment. For example, treatment tools, such as forceps or a contrast tube, are used in duodenoscopes, and treatment tools, such as a puncturing needle, are used in ultrasonic endoscopes. In such treatment tools, it is necessary to change a delivery direction of a treatment tool delivered from a treatment tool delivery port in order to treat a desired position within a subject. For this reason, the distal end member is provided with a forceps elevator (hereinafter also referred to as an "elevator"). Additionally, the operating part is provided with a treatment tool erection mechanism that changes the posture of the elevator between an erected position and a lodged position.

As the treatment tool erection mechanism, a wire pulling type mechanism to which a distal end part of a wire (also referred to as a forceps raising wire) is directly attached to the elevator is known (refer to JP1994-315458A (JP-H06-315458A)). This mechanism is a mechanism in which a proximal end side of the wire is coupled to an erection operating lever (also referred to as forceps raising lever) provided in the operating part, and the posture of the elevator is changed between the erected position and the lodged position by performing a push/pull operation of the wire by the erection operating lever, thereby rotating the elevator around a rotational movement shaft.

Specifically, the operating part of JP1994-315458A (JP-H06-315458A) is provided with a grip part for holding the operating part by hand and an angle knob. In this operating part, a wire opening part is provided below the grip part, a drive shaft opening part is provided in the grip part, a proximal end of the wire is delivered from a wire opening part, and a distal end of the drive shaft moved by the forceps raising lever is delivered from the drive shaft opening part. The distal end of the drive shaft and the proximal end of the wire are detachably coupled to a connection tool having a set screw.

Meanwhile, in a case where the endoscopes shown in JP1994-315458A (JP-H06-315458A) and EP1759626B are used for various kinds of examination or treatment, a body fluid adheres to the distal end member of the insertion part including the elevator and a guide tube through which the wire is inserted. Thus, after use, the endoscopes are subjected to cleaning and disinfection treatment, using a cleaning liquid and a disinfectant solution. In that case, the diameter of the guide tube is small and the wire is inserted through the guide tube. Therefore, in order to obtain a sufficient cleaning effect, substantial time and effort are taken for cleaning.

Thus, in the endoscope of JP1994-315458A (JP-H06-315458A), the cover, which covers the distal end member of the insertion part, the elevator, and the wire are attachably and detachably provided, the cover, the elevator, and the wire are detached, and the distal end member of the insertion part and the guide tube of the wire are cleaned.

Meanwhile, EP1759626B discloses an endoscope in which a proximal end of a cable cord is delivered from the proximal end of the control handle, and a collet is connected to a proximal end of the cable cord. The collet is fastened to a nut and is moved in a forward-backward direction by the operating lever.

SUMMARY OF THE INVENTION

However, the endoscope of JP1994-315458A (JP-H06-315458A) has a configuration in which the connection tool (hereinafter referred to as a "slider"), which connects the proximal end side of the wire to the erection operating lever side, is housed in a narrow interior of the operating part, and the set screw is rotated to connect the proximal end side of the wire to the slider. Thus, there is a problem that the attachment and detachment work of the proximal end side of the wire with respect to the slider becomes complicated.

Meanwhile, in the endoscope of EP1759626B, the cable cord is delivered to the outside of the control handle, and the distal end of the cable cord is attachably and detachably mounted to the collet and the nut. However, the attachment and detachment work is complicated.

The invention has been made in view of such circumstances, and an object thereof is to provide an endoscope that can easily perform the attachment and detachment work of a proximal end side of a wire with respect to a slider.

In order to achieve the object of the invention, the endoscope of the invention comprises an operating part that is provided with an operating member; an insertion part that is provided on a distal end side of the operating part and is inserted into a subject; a forceps elevator (elevator) that is provided at a distal end part of the insertion part; an erection operating wire that is disposed to be inserted through a wire insertion passage formed from the operating part to the insertion part so as to be movable forward and backward and is attachably and detachably coupled to the forceps elevator (elevator) on a distal end side thereof; a base member that is provided in the operating part and forms a slider housing space that is independent of an internal space of the operating part; an opening part that is provided at a proximal end of the wire insertion passage and delivers a proximal end side of the erection operating wire to the slider housing space; a slider that is disposed in the slider housing space and is movable forward and backward in a longitudinal direction of the operating part depending on an operation of the operating member; an engaged part that is provided in the slider and is recessed or protrudes toward a lateral side orthogonal to a movement direction of the slider; and an engaging member that is provided at a proximal end of the erection operating wire and is pushed into and engageable with the engaged part from the lateral side.

In the invention, the slider, which moves in the longitudinal direction so as to be movable forward and backward, also includes a form in which the slider moves forward and backward in a direction inclined with respect to the longitudinal direction in addition to a form in which the slider moves forward and backward in a direction parallel to the longitudinal direction. That is, a form in which the slider moves forward and backward in a direction having a component of the longitudinal direction is included.

In one aspect of the invention, it is preferable that the engaged part has an engagement receiving part that extends linearly in the movement direction of the slider, and a positioning receiving part that is provided at the engagement receiving part and positions the engaging member in the engaged part, and the engaging member has an engaging body part that engages with the engagement receiving part, and a positioning part that engages with the positioning receiving part.

In one aspect of the invention, it is preferable that the engaging member has a columnar part that constitutes the engaging body part, and a head part that is formed to have a larger diameter than the columnar part and constitutes the positioning part.

In one aspect of the invention, it is preferable that the slider has a guide surface that guides the positioning part to the positioning receiving part.

In one aspect of the invention, it is preferable that the engaging member has a slit-shaped sandwiching part in which the proximal end side of the erection operating wire is inserted and sandwiched from an outer surface side of the engaging member.

In one aspect of the invention, it is preferable that the engaging member is a spherical body that engages with the engaged part, and the sandwiching part includes a semicircular slit formed inward from an outer surface of the spherical body.

In one aspect of the invention, it is preferable that a bottom surface of the slit reaches the center of the spherical body.

In one aspect of the invention, it is preferable to comprise a locking mechanism that is switchable between a locked position where release of an engaged state between the engaging member and the engaged part is prevented and an unlocked position where the release of the engaged state between the engaging member and the engaged part is allowed.

In one aspect of the invention, it is preferable that the locking mechanism comprises a locking member that is provided on any one of the engaging member and the slider, and a locking recess that is provided on the other of the engaging member and the slider and engages with the locking member, and wherein the locked position is reached in a case where the locking member and the locking recess are engaged with each other, and the unlocked position is reached in a case where the engagement between the locking member and the locking recess is released.

In order to achieve the object of the invention, the endoscope of the invention comprises an operating part that is provided with an operating member; an insertion part that is provided on a distal end side of the operating part and is inserted into a subject; a forceps elevator (elevator) that is provided at a distal end part of the insertion part; an erection operating wire that is disposed to be inserted through a wire insertion passage formed from the operating part to the insertion part so as to be movable forward and backward and is attachably and detachably coupled to the forceps elevator (elevator) on a distal end side thereof; a base member that is provided in the operating part and forms a slider housing space that is independent of an internal space of the operating part; an opening part that is provided at a proximal end of the wire insertion passage and delivers a proximal end side of the erection operating wire to the slider housing space; a slider that is disposed in the slider housing space and is movable forward and backward in a longitudinal direction of the operating part depending on an operation of the operating member; an engaged part that is provided in the slider and is recessed or protrudes toward a lateral side orthogonal to a movement direction of the slider; and an engaging member that is pushed into and engageable with the engaged part from the lateral side and sandwiches and fixes the proximal end side of the erection operating wire between the engaging member and the engaged part.

In one aspect of the invention, it is preferable to comprise a locking mechanism that is switchable between a locked position where release of an engaged state between the engaging member and the engaged part is prevented and an unlocked position where the release of the engaged state between the engaging member and the engaged part is allowed.

In one aspect of the invention, it is preferable that the locking mechanism comprises a cam engaging part that is provided on any one of the engaging member and the engaged part, and a cam groove that is provided on the other of the engaging member and the engaged part and engages with the cam engaging part, and wherein the engaging member and the engaged part are engaged with each other and reaches the locked position as the cam engaging part is pushed into the cam groove while being guided by the cam groove.

According to the invention, the attachment and detachment work of the proximal end side of the wire with respect to the slider can be easily performed.

BRIEF DESCRIPTION OF THE DRAWINGS

FIG. 15 is an explanatory view illustrating a state where the proximal end side of the wire is connected to the slider.

DESCRIPTION OF THE PREFERRED EMBODIMENTS

Hereinafter, preferred embodiments of an endoscope according to the invention will be described with reference to the accompanying drawings.

Figure 1:
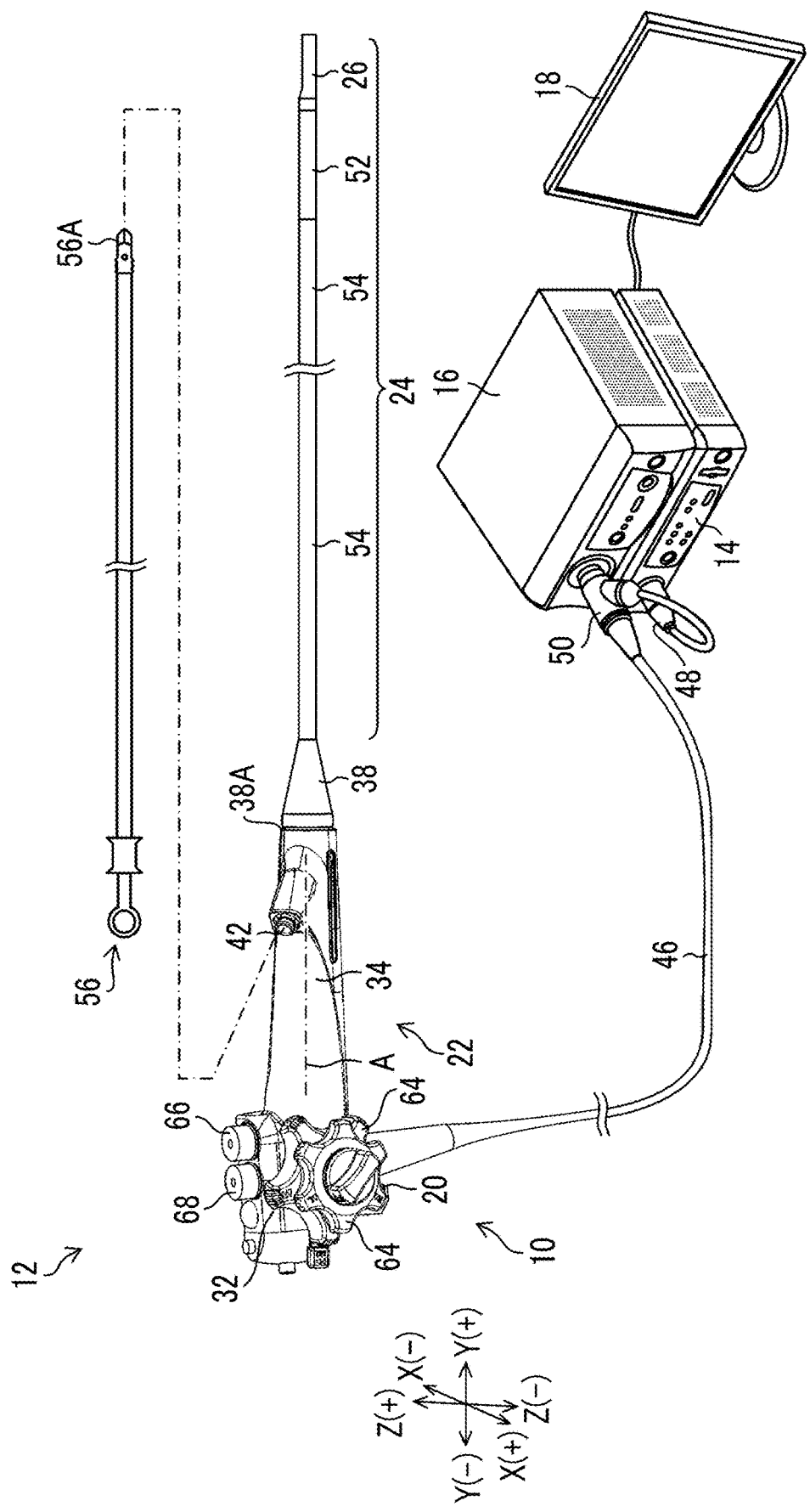
FIG. 1 is a configuration view of an endoscope system comprising an endoscope according to an embodiment.

FIG. 1 is a configuration view of an endoscope system 12 comprising an endoscope 10 according to an embodiment of the invention. The endoscope system 12 comprises the endoscope 10, a processor device 14, a light source device 16, and a display 18. In addition, a treatment tool 56 to be used in the endoscope system 12 is also illustrated in FIG. 1.

The endoscope 10 comprises an operating part 22 in which an erection operating lever 20 is provided, and an insertion part 24 that is provided on a distal end side of the operating part 22 and is inserted into a subject. The erection operating lever 20 is equivalent to an operating part of the invention.

Figure 2:
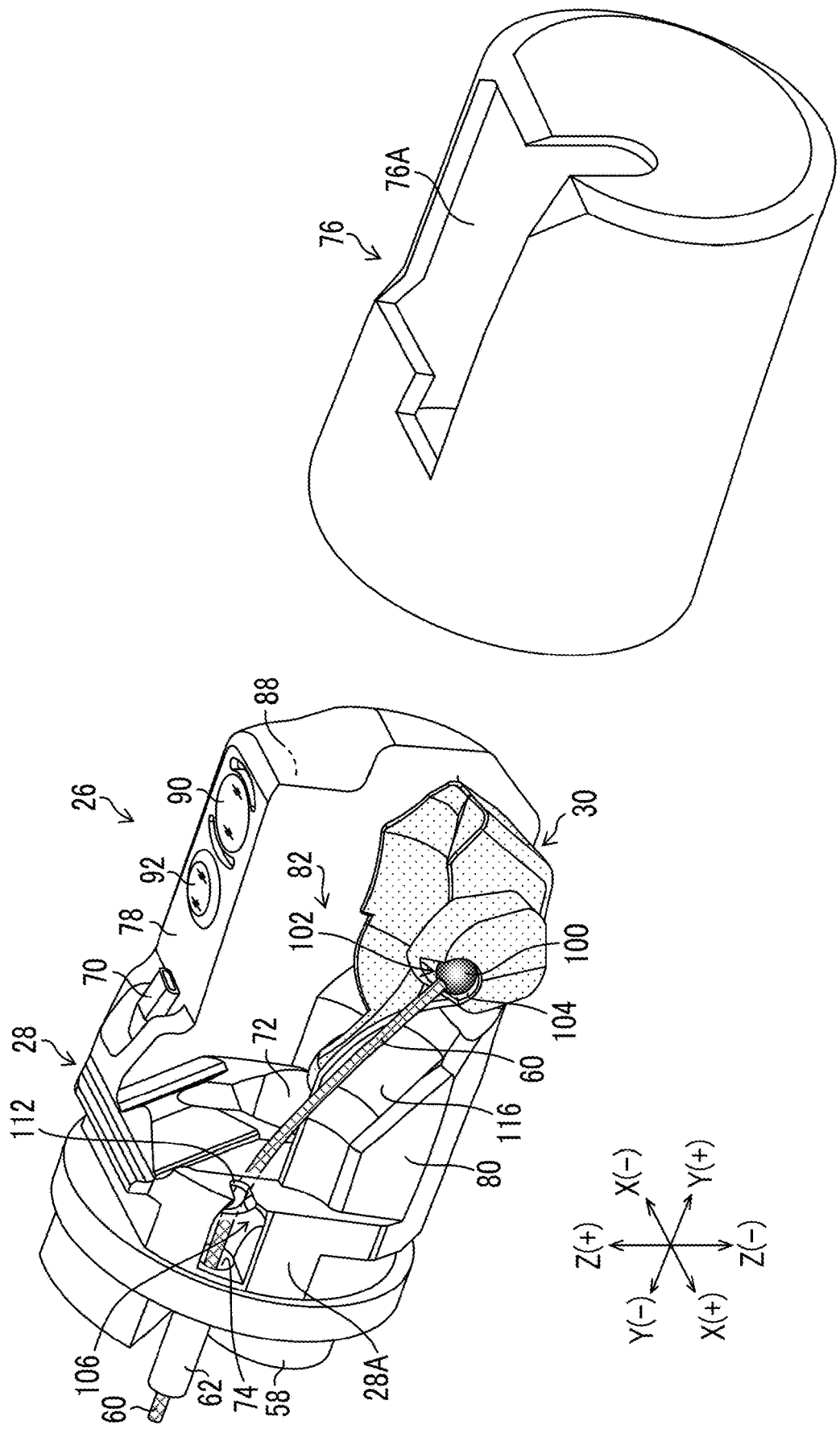
FIG. 2 is a perspective view of a distal end member where an elevator is located at a lodged position.
Figure 3:
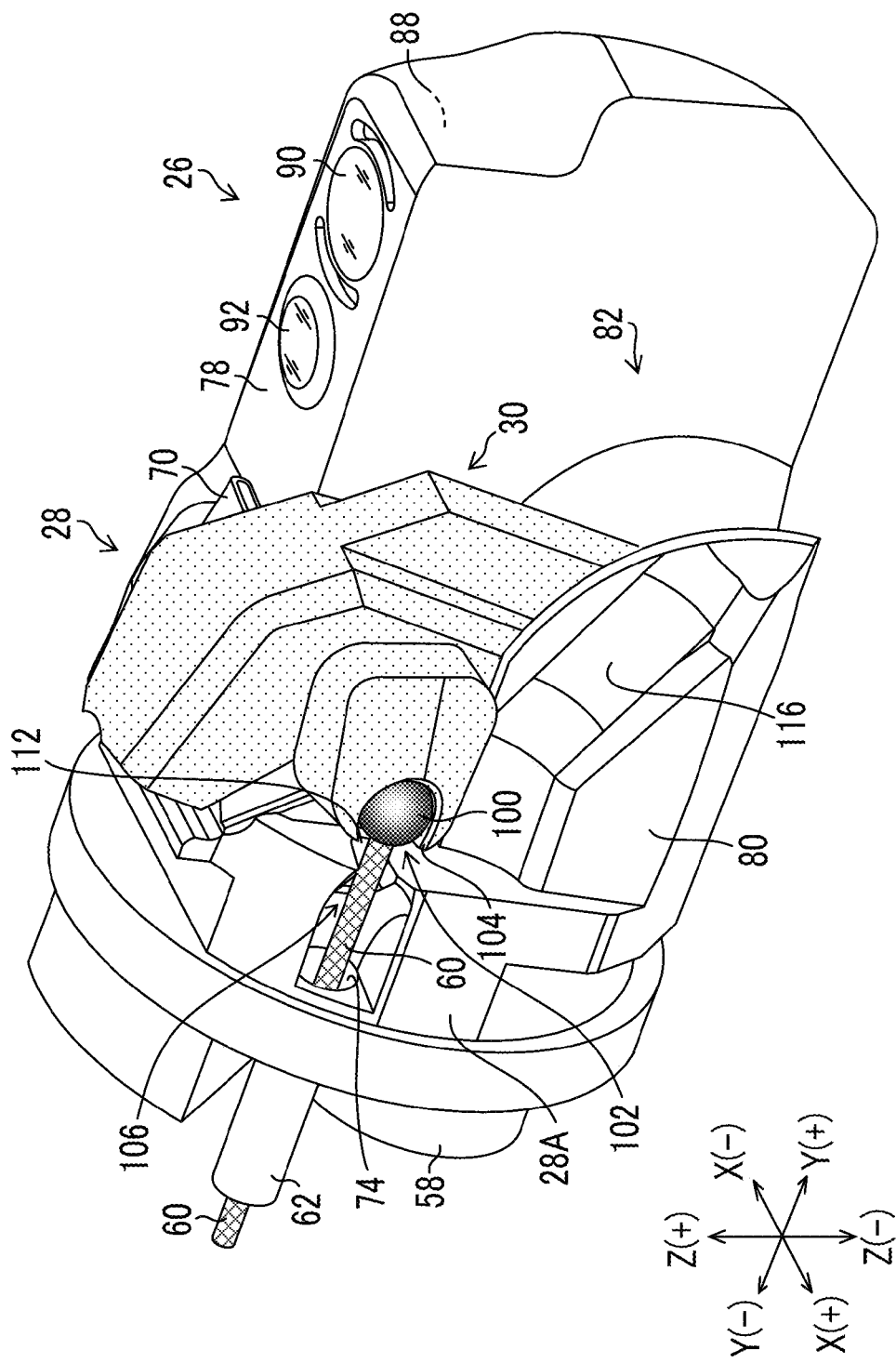
FIG. 3 is a perspective view of the distal end member where the elevator is located at an erected position.

Additionally, as illustrated in perspective views of FIGS. 2 and 3 illustrating the configuration of a distal end part 26 of the insertion part 24, a distal end part 26 of the insertion part 24 is provided with a distal end member 28, and the distal end member 28 is provided with an elevator 30 to be described below. FIG. 2 is a perspective view of the distal end member 28 where the elevator 30 is located at a lodged position, and FIG. 3 is a perspective view of the distal end member 28 where the elevator 30 is located at an erected position.

In addition, in the following description, an upward direction refers to a Z(+) direction of FIGS. 1 and 2, and a downward direction refers to a Z(−) direction of FIGS. 1 and 2. Additionally, a rightward direction refers to an X(+) direction of FIG. 2, and a leftward direction refers to an X(−) direction of FIG. 2. Moreover, a Y(+) direction of FIGS. 1 and 2 refers to a distal-end-side direction of the distal end member 28, and a Y(−) direction of FIGS. 1 and 2 refers to a proximal-end-side direction of the distal end member 28.

As illustrated in FIG. 1, the operating part 22 has an operating part body 32 provided with the erection operating lever 20, and a gripping part 34 continuously connected to the operating part body 32. The insertion part 24 is provided at a distal end part of the gripping part 34 via a folding-preventing tube 38. In addition, the gripping part 34 is a portion gripped by a surgeon in a case where the endoscope 10 is operated.

The operating part body 32 of the operating part 22 is provided with a universal cord 46. A light source connector 50 is provided on a distal end side of the universal cord 46. An electric connector 48 is provided so as to branch from the light source connector 50. The electric connector 48 is connected to the processor device 14, and the light source connector 50 is connected to the light source device 16.

The insertion part 24 is configured such that the distal end part 26, a bending part 52, and a flexible part 54 are coupled to each other from a distal end side toward a proximal end side.

The following contents are provided inside the insertion part 24. That is, contents, such as a treatment tool channel 58 that guides a distal end part 56A of the treatment tool 56 of FIG. 1 to the distal end member 28 of FIG. 2, an erection operating wire 60 (hereinafter referred to as a wire 60) for performing the operation of changing the delivery direction of the distal end part 56A of the treatment tool 56 delivered from the distal end member 28, an erection operating wire channel 62 (a wire channel 62 hereinafter referred to as) for guiding a distal end of the wire 60 to the distal end member 28, a light guide (not illustrated) that guides the illumination light, which is supplied from the light source device 16 of FIG. 1, to the distal end member 28 of FIG. 2, an air/water supply tube (not illustrated), an angle wire (not illustrated), and a signal cable (not illustrated) are provided. The wire channel 62 is an example of a wire insertion passage of the invention formed from the operating part 22 to the insertion part 24, and the wire 60 is disposed to be inserted through the wire channel 62 so as to be movable forward and backward.

Referring back to FIG. 1, the operating part 22 is formed in a substantially cylindrical shape as a whole and has a longitudinal axis A in a Y(+)-Y(−) direction. Additionally, a pair of angle knobs 64 and 64, which bends the bending part 52, is disposed in the operating part 22. The pair of angle knobs 64 and 64 is provided on the same axis in a rotationally movable manner.

The bending part 52 has a structural body in which a plurality of angle rings (not illustrated) are coupled to each other in a rotationally movable manner. The bending part 52 is configured by covering an outer periphery of the structural body with a tubular net knit with metal wires and covering an outer peripheral surface of the net with a tubular outer cover made of rubber. For example, four angle wires (not illustrated) are disposed from the bending part 52 configured in this way to the angle knobs 64 and 64, and the bending part 52 is bent upward, downward, and rightward, and leftward by pushing and pulling of the angle wires by the rotational movement operation of the angle knobs 64 and 64.

An air/water supply button 66 and a suction button 68 are provided side by side by the operating part body 32 of the operating part 22. By operating the air/water supply button 66, air and water can be sprayed from an air/water supply nozzle 70 provided in the distal end member 28 of FIG. 2. Additionally, by operating the suction button 68 of FIG. 1, a body fluid, such as blood, can be suctioned from a suction port that also serves as a treatment tool delivery port 72 provided in the distal end member 28 of FIG. 2.

Moreover, the gripping part 34 of the operating part 22 of FIG. 1 is provided with a treatment tool introduction port 42 that introduces the treatment tool 56. The treatment tool 56, which is introduced with the distal end part 56A as a head from the treatment tool introduction port 42, is inserted through the treatment tool channel 58 of FIG. 2 inserted through the insertion part 24 and is delivered from the treatment tool delivery port 72 provided in the distal end member 28 to the outside.

Figure 9:
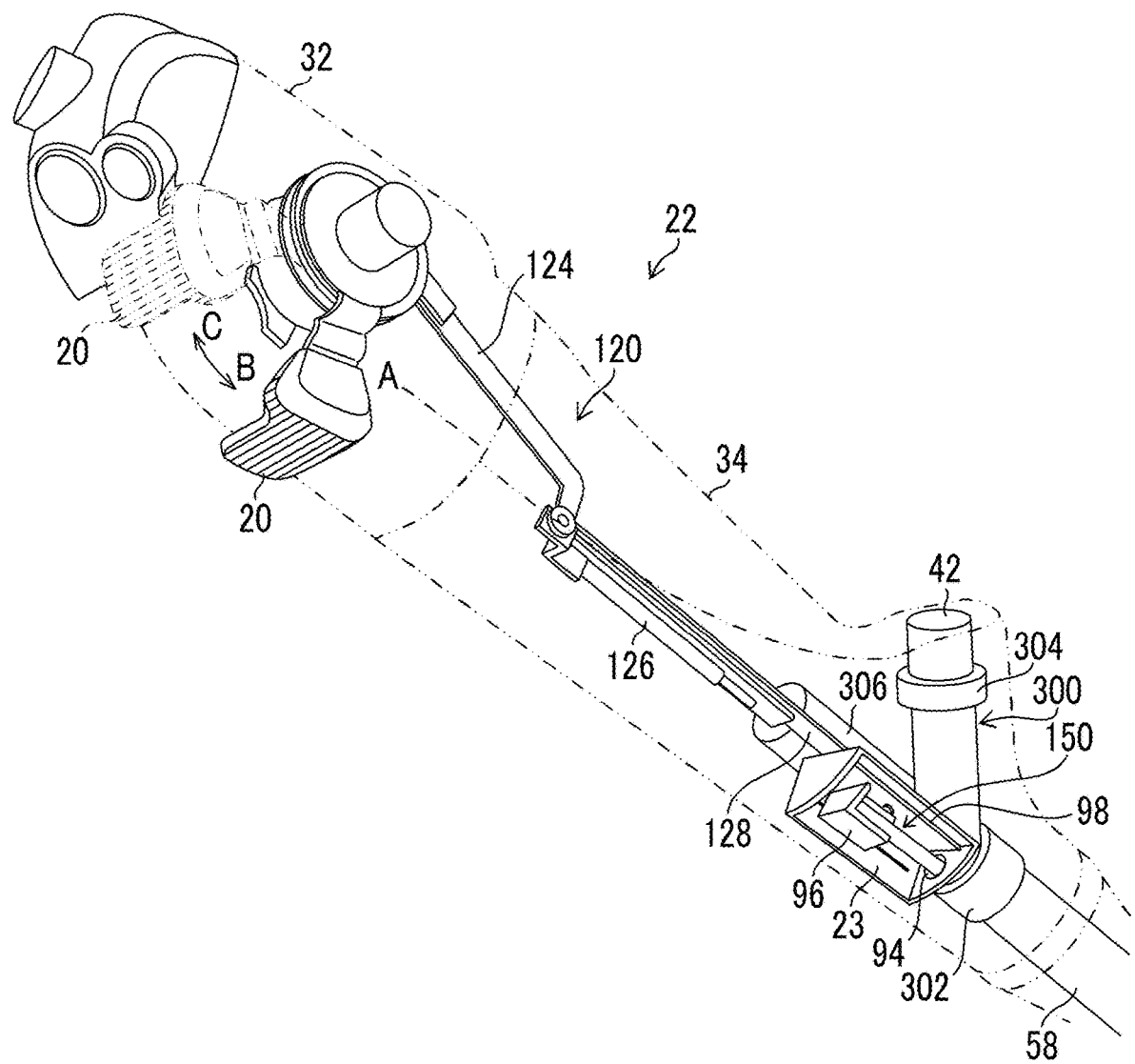
FIG. 9 is a perspective view illustrating the configuration of an erection operating mechanism.

Moreover, the erection operating lever 20 is rotatably provided in the operating part 22 of FIG. 1 coaxially with angle knobs 64 and 64. The erection operating lever 20 is rotationally operated by a surgeon's hand that grips the gripping part 34. In a case where the erection operating lever 20 is rotationally operated, the wire 60 of FIG. 2 is pushed and pulled by an erection operating mechanism 120 (refer to FIG. 9) and a slider 96 (refer to FIG. 9) that are operated in conjunction with the rotational operation of the erection operating lever 20. As the wire 60 is pushed and pulled, the posture of the elevator 30 coupled to the distal end of the wire 60 is changed between the erected position of FIG. 3 and the lodged position of FIG. 2. In addition, the erection operating mechanism 120 and the slider 96 that are illustrated in FIG. 9 will be described below.

Referring back to FIG. 1, the flexible part 54 has a spiral tube (not illustrated) obtained by spirally winding a thin metallic beltlike sheet having elasticity. The flexible part 54 is configured by covering the outside of the spiral tube with a tubular net knit with metal wires and covering an outer peripheral surface of the net with a tubular outer cover from a resin.

The endoscope 10 of the embodiment configured as described above is a side viewing endoscope used as a duodenoscope, and the insertion part 24 is inserted into the subject via an oral cavity. The insertion part 24 is inserted from the esophagus through the stomach to the duodenum, and treatment, such as a predetermined examination or curing, is performed.

In addition, in the embodiment, biopsy forceps having a cup capable of collecting a biological tissue at the distal end part 56A has been exemplified as the treatment tool 56, but the invention is not limited to this. For example, treatment tools, such as a contrast tube or a knife for endoscopic sphincterotomy (EST), are used as other treatment tools.

Next, the structure of the distal end part 26 of the insertion part 24 will be described.

As illustrated in FIG. 2, the distal end part 26 of the insertion part 24 is constituted of the distal end member 28, and a cap 76 that is attachably and detachably mounted to the distal end member 28. The cap 76 is formed in a substantially tubular shape that is sealed on a distal end side thereof, and a substantially rectangular opening window 76A is formed in a portion of an outer peripheral surface of the cap 76. In a case where the cap 76 is mounted on the distal end member 28, the opening window 76A of the cap 76 communicates with the treatment tool delivery port 72 of the distal end member 28. As a result, the distal end part 56A of the treatment tool 56 delivered from the treatment tool delivery port 72 is delivered from the opening window 76A to the outside.

The cap 76 is made of a material with an elastic force, for example, a rubber material, such as fluororubber or silicone rubber, or a resin material, such as polysulfone. An engaging part (not illustrated) engaging with a groove (not illustrated) formed in the distal end member 28 is provided on a proximal end side of the cap 76, and the cap 76 is mounted on the distal end member 28 by engaging this engaging part with the groove of the distal end member 28. Additionally, in a case where the treatment of the endoscope 10 is completed, the cap 76 is detached from the distal end member 28 and cleaned and disinfected or is discarded as a disposable.

The distal end member 28 is made of a metallic material having corrosion resistance. Additionally, a partition wall 78 provided to protrude toward the distal end side and a partition wall 80 that faces the partition wall 78 are integrally provided in the distal end member 28. An elevator housing chamber 82 that houses the elevator 30 is formed between the partition wall 78 and the partition wall 80. The treatment tool delivery port 72 for delivering the treatment tool 56 to the outside is formed on a proximal end side of the elevator housing chamber 82, and a distal end part of the treatment tool channel 58 is connected to the treatment tool delivery port 72.

The treatment tool channel 58 is inserted through the insertion part 24 of FIG. 1. A proximal end part of the treatment tool channel 58 is connected to a distal end tube 302 of a branched tube 300 (refer to FIG. 9) provided inside the operating part 22.

The branched tube 300 has a well-known structure, a proximal end part thereof is branched to two pipe lines 304 and 306, and the treatment tool introduction port 42 is formed at a proximal end of one pipe line 304. Therefore, the distal end part 56A of the treatment tool 56 introduced from the treatment tool introduction port 42 is inserted through the treatment tool channel 58 via the pipe line 304 and is delivered from the treatment tool delivery port 72 of FIG. 2 to the elevator housing chamber 82. Then, the distal end part 56A of the treatment tool 56 delivered to the elevator housing chamber 82 is changed in delivery direction depending on the posture between the erected position and the lodged position of the elevator 30 disposed in the elevator housing chamber 82. Additionally, a distal end of a suction tube (not illustrated) that suctions a body fluid, such as blood, is connected to a proximal end of the other pipe line 306 of the branched tube 300 illustrated in FIG. 9.

Figure 4:
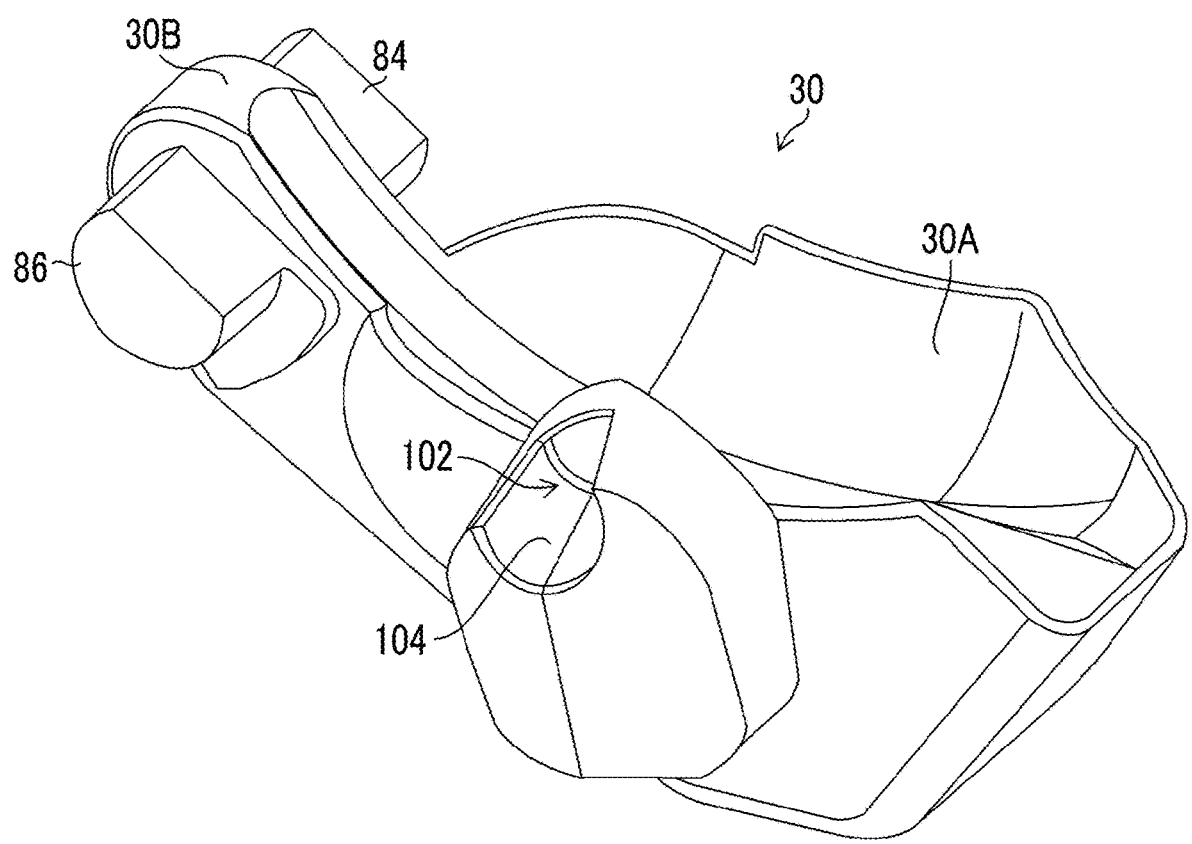
FIG. 4 is an enlarged perspective view of the elevator.

FIG. 4 is an enlarged perspective view of the elevator 30. As illustrated in FIG. 4, an upper surface of the elevator 30 is provided with a guide surface 30A. The distal end part 56A of the treatment tool 56 of FIG. 1 is delivered from the opening window 76A of the cap 76 of FIG. 2 to the outside along the guide surface 30A.

As illustrated in FIG. 4, both side surfaces of a proximal part 30B of the elevator 30 are provided with rotational movement shafts 84 and 86. An axial direction of the rotational movement shafts 84 and 86 is set as an X(+)-X(−) direction of FIG. 2 in a case where the elevator 30 is attached to the distal end member 28.

Figure 5:
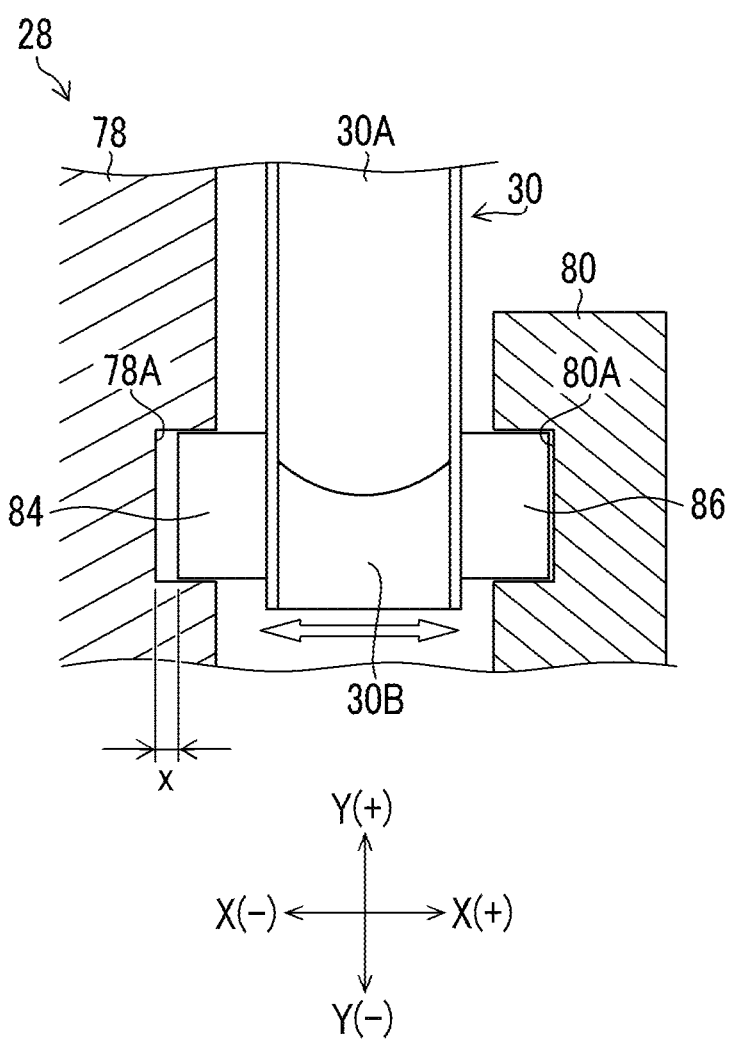
FIG. 5 is a cross-sectional view of main parts illustrating an attachment structure of the elevator with respect to the distal end member.

FIG. 5 is a cross-sectional view of main parts illustrating an attachment structure of the elevator 30 with respect to the distal end member 28. As illustrated in FIG. 5, the axes of the rotational movement shafts 84 and 86 are coaxially disposed via the proximal part 30B of the elevator 30, the rotational movement shaft 84 is fitted to a concave bearing part 78A of the partition wall 78 in a rotationally movable manner, and the rotational movement shaft 86 is fitted to a concave bearing part 80A of the partition wall 80 in a rotationally movable manner. Additionally, the rotational movement shafts 84 and 86 are mounted on the bearing parts 78A and 80A, respectively, with a predetermined rattling amount x in the axial direction of the rotational movement shafts 84 and 86. In a case where the rotational movement shafts 84 and 86 are biased to one side by utilizing the rattling amount x, a portion of one bearing part of the bearing parts 78A and 80A can be exposed and a brush can be easily inserted into the exposed portion. Thus, the cleaning performance of the bearing parts 78A and 80A is improved.

Meanwhile, as illustrated in FIGS. 2 and 3, an optical system housing chamber 88 is provided inside the partition wall 78. An illumination window 90 and an observation window 92 are disposed adjacent to each other at an upper part of the optical system housing chamber 88, and the air/water supply nozzle 70 directed to the observation window 92 is provided in the distal end member 28. The air/water supply nozzle 70 is connected to an air/water supply device (not illustrated) via the air/water supply tube (not illustrated) inserted through the insertion part 24, and air or water is sprayed from the air/water supply nozzle 70 toward the observation window 92 by operating the air/water supply button 66 of the operating part 22 illustrated in FIG. 1. As a result, the observation window 92 is cleaned.

An illumination unit (not illustrated) and an imaging unit (not illustrated) are housed inside the optical system housing chamber 88. The illumination unit comprises an illumination lens (not illustrated) installed inside the illumination window 90, and the light guide (not illustrated) disposed such that a distal end surface thereof faces the illumination lens. The light guide is disposed in the universal cord 46 via the operating part 22 from the insertion part 24 of the endoscope 10, and has a proximal end connected to the light source device 16 via the light source connector 50. As a result, the radiated light from the light source device 16 is transmitted via the light guide and is radiated from the illumination window 90 to the outside.

The aforementioned imaging unit comprises an imaging optical system (not illustrated) disposed inside the observation window 92, and a complementary metal oxide semiconductor (CMOS) type or charge coupled device (CCD) type image pickup element (not illustrated). The image pickup element is connected to the processor device 14 via the signal cable (not illustrated) inserted through the insertion part 24 of FIG. 1. After image pickup signals of a subject image obtained by the imaging unit is output to the processor device 14 via the signal cable and subjected to image processing, the image pickup signals are displayed as the subject image on the display 18.

Figure 6:
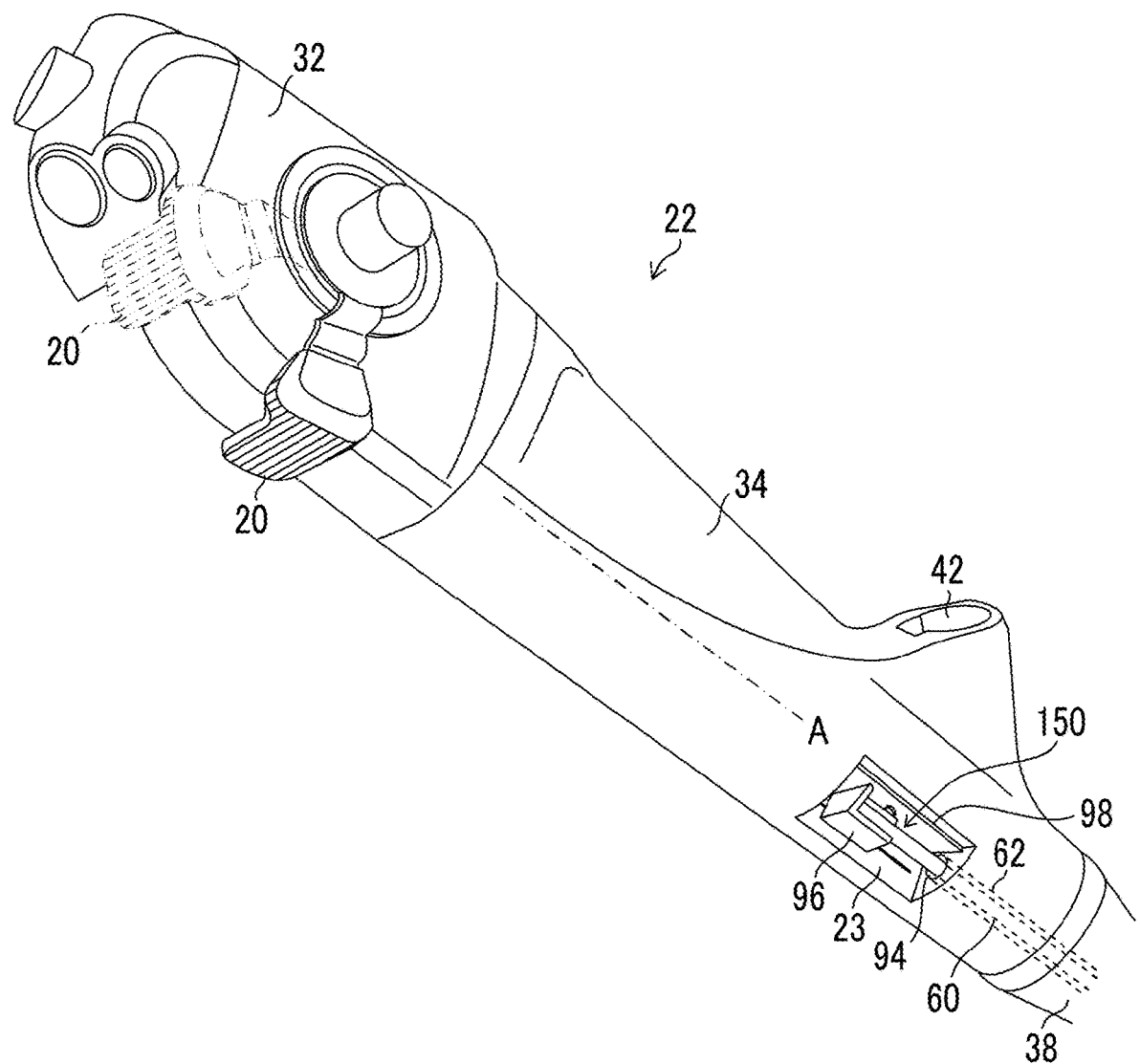
FIG. 6 is a perspective view illustrating the other side surface that faces one side surface of an operating part illustrated in FIG. 1.

Although overlapping the previous description, as for the wire 60 illustrated in FIGS. 2 and 3, the distal end of the wire 60 is disposed outside the delivery port 74 and is coupled to the elevator 30 in an engageable and disengageable manner. Additionally, as illustrated in FIG. 6, a proximal end side of the wire 60 is delivered from an opening part 94 provided in the operating part 22 to a slider housing space 150 and is coupled to the slider 96. The opening part 94 is provided at a proximal end of the wire channel 62. Additionally, the slider 96 is disposed in the slider housing space 150. The slider housing space 150 is a space that is independent of an internal space of the operating part 22 and is formed by a base member 98 provided in the operating part 22. The base member 98 and the slider housing space 150 will be described below. FIG. 6 is a perspective view of the operating part 22 of FIG. 1 as viewed upward from below.

Next, an engaging structure in which the distal end of the wire 60 engages with the elevator 30 in an engageable and disengageable manner will be described.

As illustrated in FIGS. 2 and 3, the distal end of the wire 60 is provided with an engaging member 100. Additionally, the elevator 30 is provided with a housing groove 102 that is engaged with the engaging member 100 in an engageable and disengageable manner and is formed with an opening 104 on the X(+) direction side. As a result, the distal end of the wire 60 is coupled to the elevator 30 by housing the engaging member 100 provided at the distal end of the wire 60 in the housing groove 102 via the opening 104.

In the embodiment, the engaging member 100 is a spherical body, and the housing groove 102 is a spherical recess that houses the spherical engaging member 100. In addition, although the shapes of the engaging member 100 and the housing groove 102 are not limited to the above shapes, the sliding resistance between the engaging member 100 and the housing groove 102 that occurs due to the push/pull operation of the wire 60 can be reduced by forming the engaging member 100 as a spherical body and forming the housing groove 102 as a spherical recess. Therefore, the push/pull operation of the wire 60 can be smoothly performed.

Additionally, the distal end member 28 is provided with an engagement guide part 106 provided continuously with the housing groove 102 at the erected position of FIG. 3. The engagement guide part 106 has the function of guiding the engaging member 100, which is delivered from the delivery port 74, to the opening 104 of the housing groove 102. The delivery port 74 is provided in the distal end member 28 and communicates with the opening part 94 (refer to FIG. 6) of the proximal end of the wire channel 62 via the wire channel 62.

According to the endoscope 10 having such an engagement guide part 106, in a case where the wire 60 is introduced with the engaging member 100 as a head from the opening part 94 of the wire channel 62, the engaging member 100 is inserted through the wire channel 62 (refer to FIG. 2) and is delivered from the delivery port 74 to the outside. Then, the engaging member 100 is guided toward the opening 104 of the housing groove 102 of the elevator 30 by the engagement guide part 106 by continuing the introduction operation of the wire 60 and is engaged with the housing groove 102 from the opening 104. As a result, according to the endoscope 10 of the embodiment, the engaging member 100 of the wire 60 can be engaged with the housing groove 102 of the elevator 30 simply by the introduction operation of the wire 60.

Figure 7:
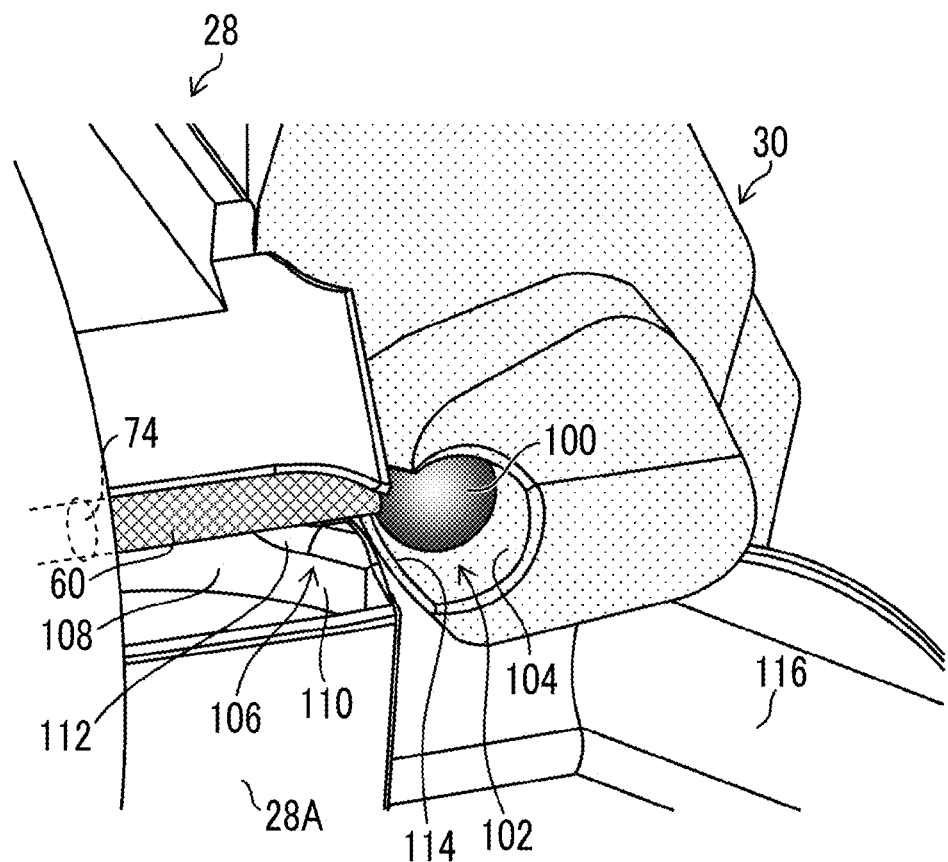
FIG. 7 is an enlarged perspective view in which an engaging part is housed in a housing part via an engagement guide part.
Figure 8:
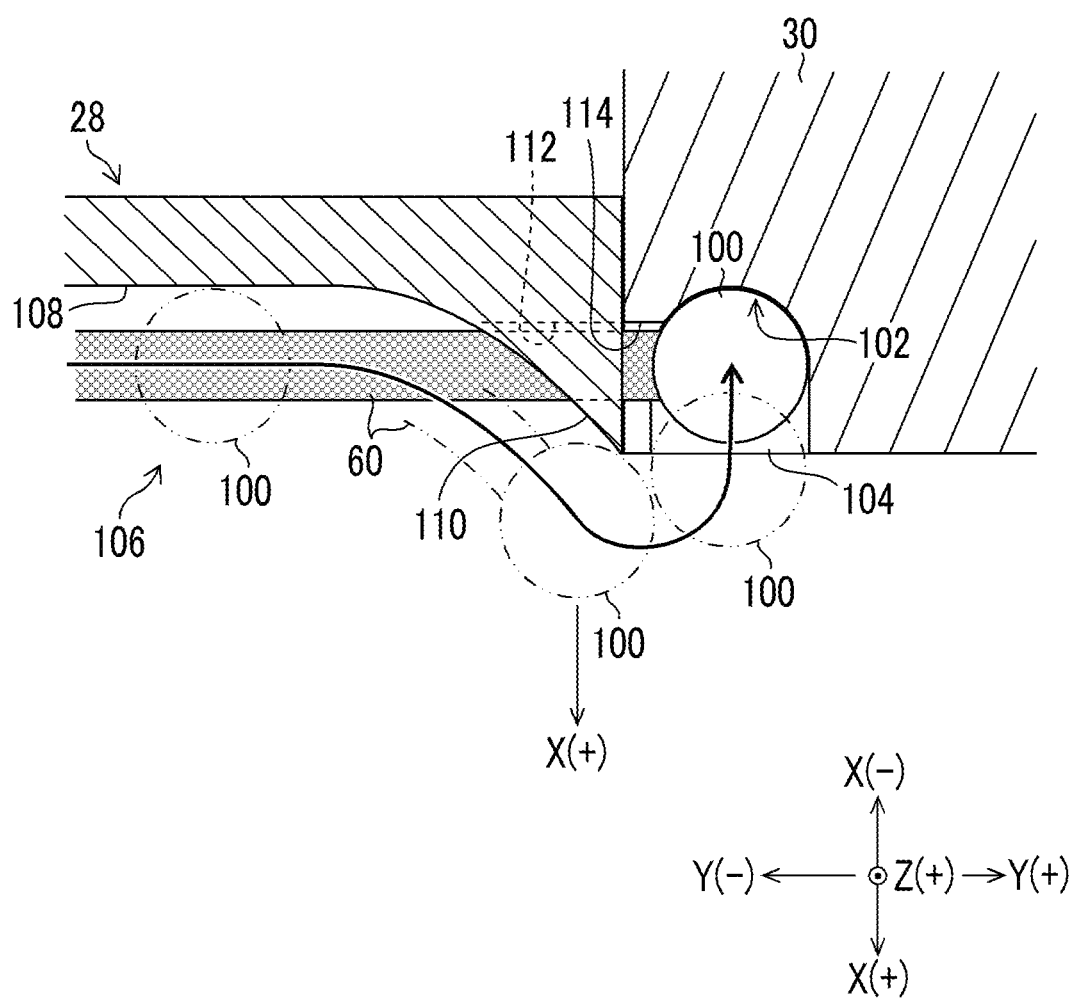
FIG. 8 is an explanatory view of the operation in which the engaging part is guided by the engagement guide part and is housed in the housing part.

FIG. 7 is an enlarged perspective view in which the engaging member 100 is engaged with the housing groove 102 via the engagement guide part 106. FIG. 8 is an explanatory view sequentially illustrating the operation until the engaging member 100 is guided to the engagement guide part 106 and engaged with the housing groove 102.

As illustrated in FIGS. 7 and 8, the engagement guide part 106 comprises an engagement guide path 108 that guides the engaging member 100, which is delivered from the delivery port 74, to the opening 104 of the housing groove 102, and a deformation generating part 110 provided continuously with the opening 104 of the housing groove 102 within the engagement guide path 108. The deformation generating part 110 comes into contact with the engaging member 100 that advances in the Y(+) direction toward the opening 104 within the engagement guide path 108 and guides the engaging member 100 in the X(+) direction while guiding the engaging member 100 in the Y(+) direction.

As a result, the distal end of the wire 60 is elastically deformed in a direction (X(+) direction) gradually away from the opening 104 as the engaging member 100 approaches the opening 104 along the engagement guide path 108. In a case where the engaging member 100 that advances within the engagement guide path 108 has passed through the deformation generating part 110, the engaging member 100 is moved in the X(−) direction by a restoring force of the wire 60 and is engaged with the housing groove 102 from the opening 104.

The engagement guide path 108 is formed by concavely cutting away a portion of a peripheral surface 28A of the distal end member 28 and is a surface that is gradually inclined in the X(+) direction from the delivery port 74 toward the Y(+) direction. The deformation generating part 110 is formed on a distal end side of the engagement guide path 108.

Additionally, a groove 112 for allowing the distal end of the wire 60 to sink and escape in a case where the engaging member 100 is engaged with the housing groove 102 is formed in the engagement guide part 106. Additionally, a groove 114 for allowing the distal end of the wire 60 to sink and escape in a case where the engaging member 100 is engaged with the housing groove 102 is also formed on a proximal end side of the housing groove 102 of the elevator 30. The width dimension of the groove 112 in a direction orthogonal to the paper plane of FIG. 8 is larger than the diameter of the wire 60 and is smaller than the diameter of the engaging member 100 such that the engaging member 100 passing through the deformation generating part 110 does not sink in the groove 112. Additionally, the width dimension of the groove 114 of in the direction orthogonal to the paper plane of FIG. 8 is larger than the diameter of the wire 60 and is smaller than the diameter of the engaging member 100 such that the engaging member 100 engaged with the housing groove 102 does not slip out in the Y(−) direction.

Additionally, the engagement guide part 106 has a form that is suitable in a case where the engaging member 100 is engaged with the housing groove 102 in a state where the elevator 30 is located at the erected position. That is, as illustrated in FIG. 7, the housing groove 102 is disposed at a position that faces the delivery port 74 in a state where the elevator 30 is located at the erected position. Therefore, by advancing the engaging member 100 straight from the delivery port 74, the engaging member 100 can be engaged with the housing groove 102 of the elevator 30 located at the erected position via the engagement guide part 106.

Next, a separation structure for separating the engaging member 100 of the wire 60 engaged with the housing groove 102 of the elevator 30 from the housing groove 102 will be described.

As illustrated in FIGS. 2 and 3, the distal end member 28 is provided with a separation guide surface 116, and the separation guide surface 116 is provided on an upper surface of the partition wall 80. The separation guide surface 116 is a guide surface that is inclined in the Z(−) direction toward the X(+) direction. Additionally, as illustrated in FIG. 2, the separation guide surface 116 functions as a surface of guiding the wire 60 in a direction in which the engaging member 100 is separated from the inside of the housing groove 102 to the outside of the opening 104 in a case where the wire 60 is further pushed in a state where the engaging member 100 is engaged with the housing groove 102 and the elevator 30 is located at the lodged position.

According to the separation structure configured in this way, the elevator 30 is located at the lodged position of FIG. 2 from the erected position of FIG. 3 by detaching the proximal end side of the wire 60 from the slider 96 of FIG. 6, and thereafter operating to push the wire 60 from the opening part 94 of the wire channel 62. Thereafter, in a case where the wire 60 is further pushed, the wire 60 is guided in the X(+) direction in which the engaging member 100 is separated from the inside of the housing groove 102 to the outside the opening 104 by the separation guide surface 116 of the distal end member 28. As a result, the engaging member 100 is easily separated from the inside of the housing groove 102 to the outside of the opening 104 by the restoring force of the wire 60.

Next, the erection operating mechanism 120 illustrated in FIG. 9 will be described.

FIG. 9 is a perspective view illustrating the configuration of the erection operating mechanism 120. In addition, in FIG. 9, a sheathing case (not illustrated) of the operating part 22 is omitted, and the inside of the operating part 22 is illustrated in a simplified manner.

In the erection operating mechanism 120 illustrated in FIG. 9, constituent elements of the respective parts that constitute the erection operating mechanism 120 are continuously provided from the operating part body 32 to the gripping part 34 inside the operating part 22.

The erection operating mechanism 120 is a power transmission mechanism that couples the erection operating lever 20 and the slider 96 to each other and transmits the rotational operation of the erection operating lever 20 to a slider 96.

The erection operating mechanism 120 comprises an arm 124 that converts the rotary motion of the erection operating lever 20 into a linear motion, a drive shaft 126 that is coupled to the arm 124 and performs a linear motion together with the arm 124, a drive arm 128 that is coupled to the drive shaft 126 and performs a linear motion together with the drive shaft 126, a first lever 130 (refer to FIG. 10) that is coupled to the drive arm 128 and converts the linear motion of the drive arm 128 into a rotary motion, and a second lever 132 (refer to FIG. 10) that is coupled to the first lever 130 and converts the rotary motion of first lever 130 into a linear motion to transmit the converted linear motion to the slider 96.

Figure 10:
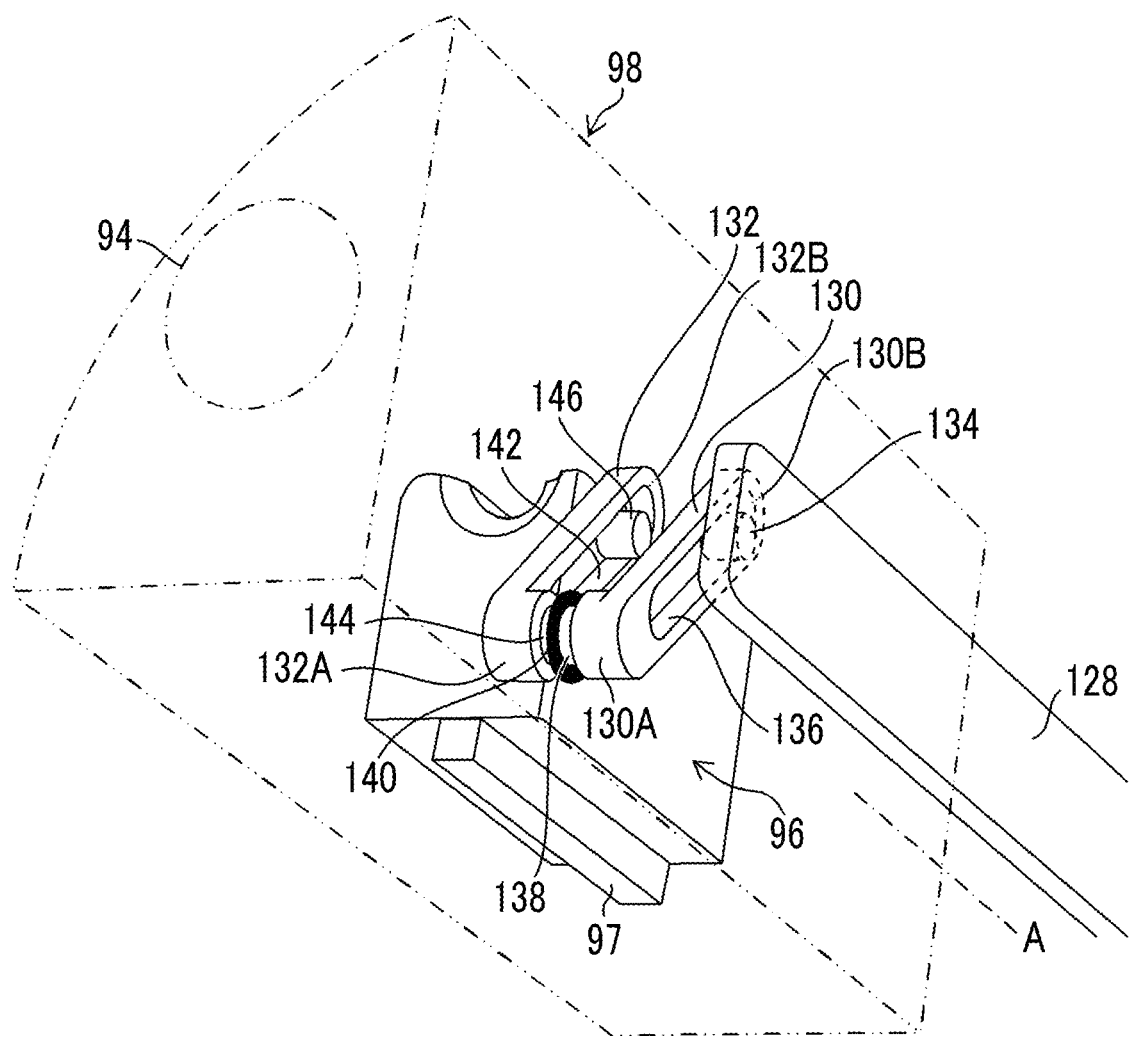
FIG. 10 is an explanatory view in which a drive arm and a slider are connected to each other via first and second levers.

FIG. 10 is an explanatory view illustrating a structure in which the drive arm 128 and the slider 96 are connected to each other via the first lever 130 and the second lever 132, and a base member 98 is illustrated by a two-dot chain line in FIG. 10.

As illustrated in FIG. 10, a cam pin 134 is provided to protrude from a distal end part of the drive arm 128, and the cam pin 134 is slidably engaged with a cam groove 136 of the first lever 130.

The first lever 130 has one end part 130A and the other end part 130B, and a linear cam groove 136 is formed from the one end part 130A to the other end part 130B. Additionally, a rotating shaft 138 is provided at the one end part 130A of the first lever 130. The rotating shaft 138 is disposed to be inserted through a through-hole (not illustrated) formed in the base member 98 and is rotatably attached to the base member 98 via an O-ring 140 provided on the rotating shaft 138. An internal space of the operating part 22 is sealed by the O-ring 140 from the slider housing space 150 illustrated in FIG. 6.

The second lever 132 of FIG. 10 is disposed in the slider housing space 150 (refer to FIG. 6). The second lever 132 is formed in the same shape as the first lever 130 and is disposed to face the first lever 130 via the base member 98.

The second lever 132 has one end part 132A and the other end part 132B, and a linear cam groove 142 is formed from the one end part 132A to the other end part 132B. Additionally, a rotating shaft 144 is provided at the one end part 132A of the second lever 132. The rotating shaft 144 is coupled to the rotating shaft 138 of the first lever 130 protruding from a through-hole (not illustrated) of the base member 98. A cam pin 146 provided to protrude from the slider 96 is slidably engaged with the cam groove 142 of the second lever 132.

Next, the operation of the erection operating mechanism 120 illustrated in FIG. 9 will be described.

In a case where the erection operating lever 20 is rotationally operated in a direction of arrow B from a position illustrated by a two-dot chain line to a position illustrated by a solid line, the arm 124 performs a linear motion toward a proximal end side of the operating part 22 along the longitudinal axis A of the operating part 22. Then, the drive shaft 126 and the drive arm 128 also perform a linear motion similarly toward the proximal end side in conjunction with the operation of the arm 124.

Figure 11:
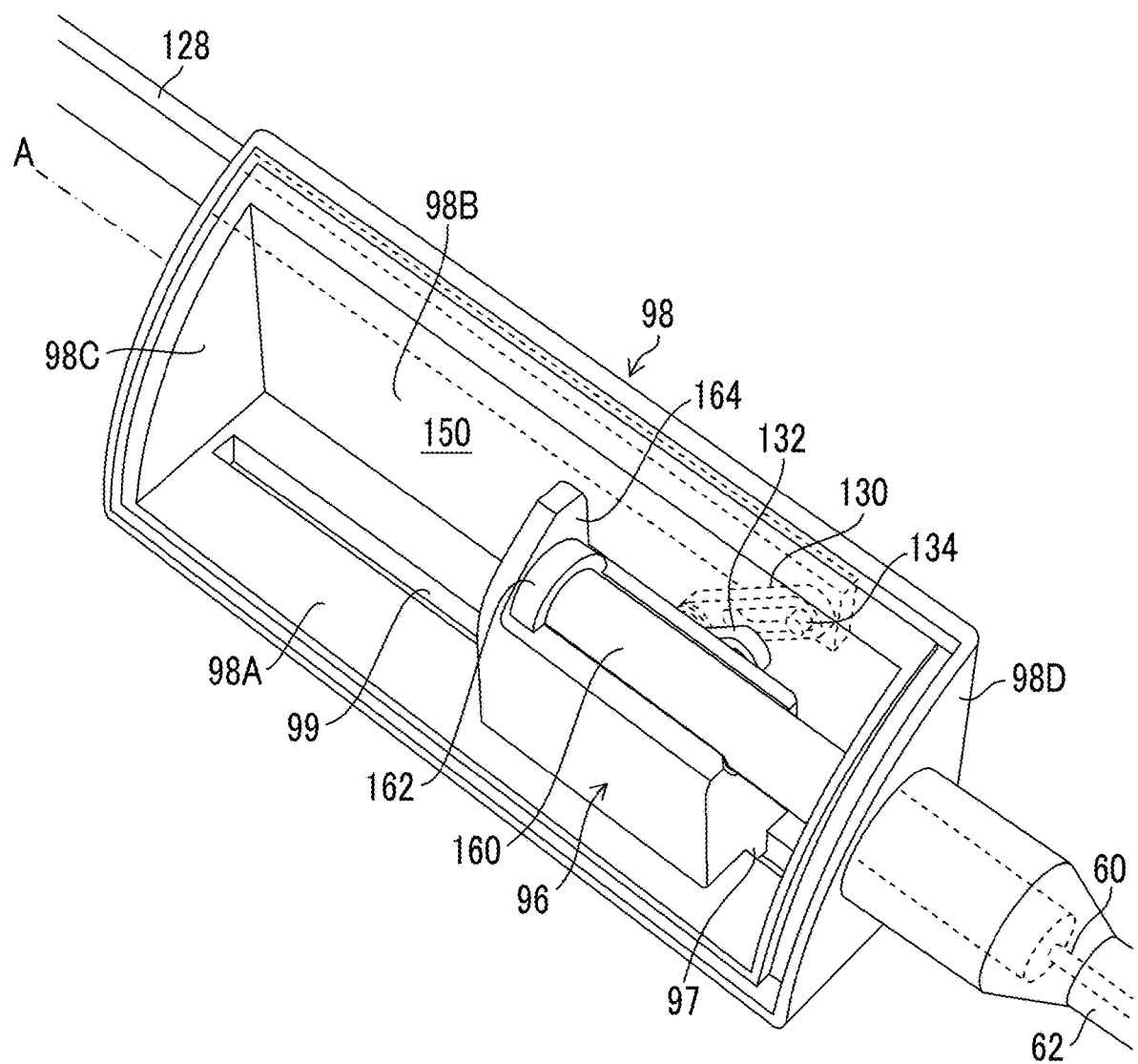
FIG. 11 is an explanatory view illustrating the position of the drive arm in a case where the elevator is located at the lodged position.

Here, FIG. 11 is an explanatory view illustrating the position of the drive arm 128 in a case where the erection operating lever 20 is located at the position illustrated by the two-dot chain line of FIG. 9, i.e., the elevator 30 is located at the lodged position (refer to FIG. 2). Additionally, FIG. 12 is an explanatory view illustrating the position of the drive arm 128 in a case where the erection operating lever 20 is located at the position illustrated by the solid line of FIG. 9, i.e., the elevator 30 is located at the erected position (refer to FIG. 3).

Figure 12:
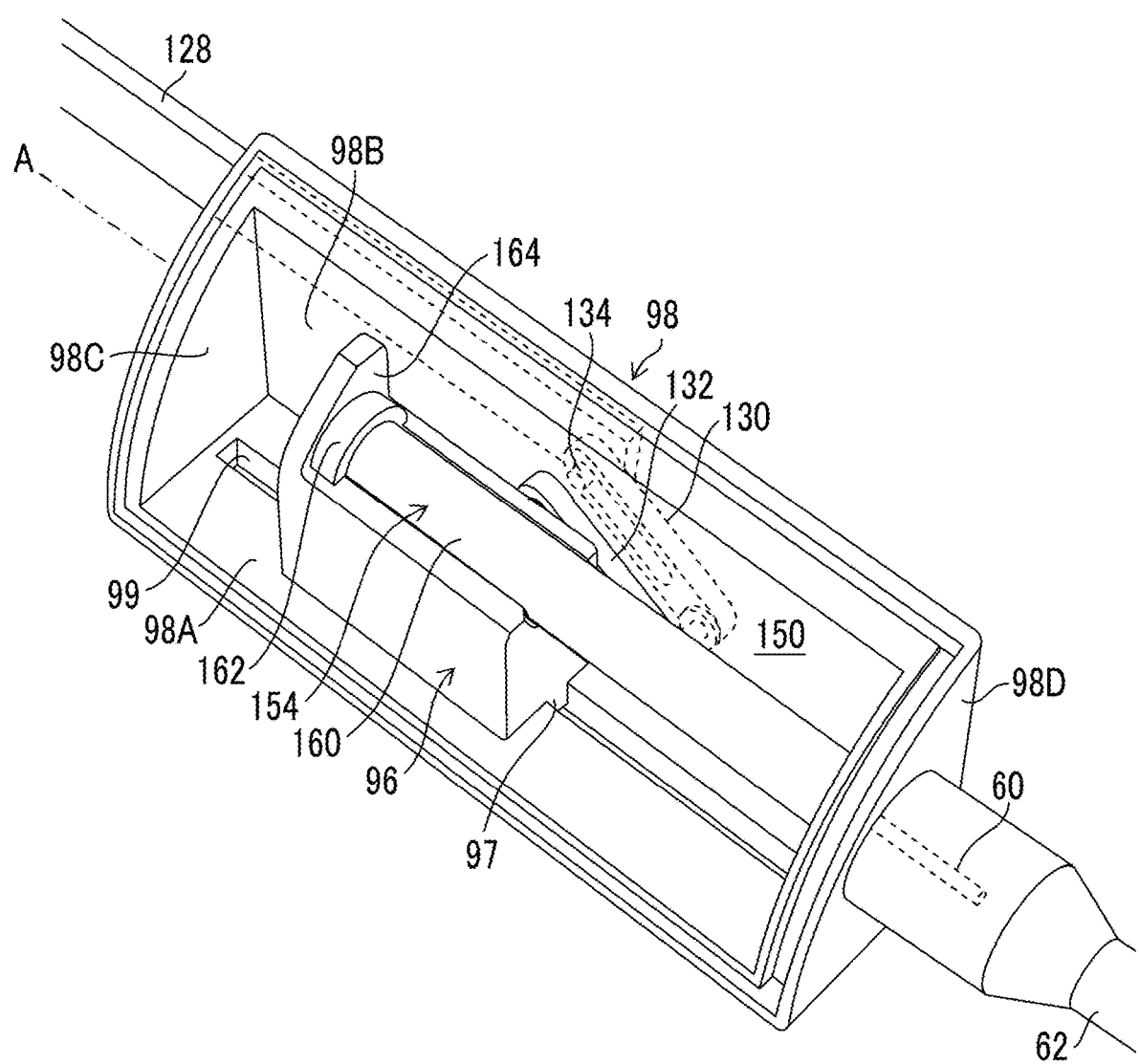
FIG. 12 is an explanatory view illustrating the position of the drive arm in a case where the elevator is located at the erected position.

In a case where the drive arm 128 performs a linear motion from the position of FIG. 11 toward the position of FIG. 12 by the operation of the erection operating lever 20, the first lever 130 rotates toward the proximal end side of the operating part 22 around the rotating shaft 138 by the action of the cam pin 134 and the cam groove 136 of FIG. 10. Then, the second lever 132 rotates toward the proximal end side of the operating part 22 around the rotating shaft 144 in conjunction with the rotation of the first lever 130. As a result, the slider 96 slidingly moves from the position of FIG. 11 toward the position of FIG. 12 along the longitudinal axis A by the action of the cam pin 146 (refer to FIG. 10) and the cam groove 142. The proximal end side of the wire 60 is coupled to the slider 96 as will be described below. Hence, in a case where the slider 96 slidingly moves from the position of FIG. 11 toward the position of FIG. 12, the wire 60 is pulled, and the elevator 30 moves to the erected position of FIG. 3.

On the other hand, contrary to this operation, in a case where the erection operating lever 20 is rotationally operated in a direction of arrow C from the position illustrated by the solid line of FIG. 9 to the position illustrated by the two-dot chain line, the arm 124 performs a linear motion toward the distal end side of the operating part 22 along the longitudinal axis A of the operating part 22. Then, the drive shaft 126 and the drive arm 128 also perform a linear motion similarly toward the distal end side in conjunction with the operation of the arm 124.

As a result, since the drive arm 128 performs a linear motion from the position of FIG. 12 toward the position of FIG. 11, the first lever 130 rotates toward the distal end side of the operating part 22 around the rotating shaft 138 by the action of the cam pin 134 and the cam groove 136. Then, the second lever 132 rotates toward the distal end side of the operating part 22 around the rotating shaft 144 in conjunction with the rotation of the first lever 130. As a result, the slider 96 slidingly moves from the position of FIG. 12 toward the position of FIG. 11 by the action of the cam pin 146 and the cam groove 142. The wire 60 is pushed by the movement of the slider 96, and the elevator 30 moves to the lodged position of FIG. 2.

The above operation is the operation of the erection operating mechanism 120. The slider 96 is moved in the longitudinal direction of the operating part 22 along the longitudinal axis A of the operating part 22 depending on the operation of the erection operating lever 20 by the erection operating mechanism 120 as to be movable forward and backward.

Next, the base member 98 will be described with reference to FIGS. 6, 11, and 12.

As illustrated in FIG. 6, the base member 98 is provided in an opening part 23 formed in the operating part 22.

Additionally, as illustrated in FIGS. 11 and 12, the base member 98 is constituted of a plate-shaped body part 98A disposed along the longitudinal axis A of the operating part 22, a wall part 98B provided in a direction orthogonal to the body part 98A on a side part of the body part 98A, a fan-shaped proximal end wall 98C that couples respective proximal end parts of the body part 98A and the wall part 98B to each other, and a fan-shaped distal end wall 98D that couples respective distal end parts of the body part 98A and the wall part 98B to each other, an opening (not illustrated) is formed in the distal end wall 98D, and the opening part 94 (refer to FIG. 6) of the wire channel 62 is disposed in this opening. The base member 98 configured in this way is provided in the opening part 23 of the operating part 22. As a result, the slider housing space 150 independent of the internal space of the operating part 22 is formed in the operating part 22.

The slider housing space 150 is a space surrounded by the body part 98A, the wall part 98B, the proximal end wall 98C, and the distal end wall 98D of the base member 98, and is a space in which a cross-sectional shape in the direction orthogonal to the longitudinal axis A is fan-shaped, as an example. As illustrated in FIG. 6, the slider housing space 150 may have a form in which the slider housing space is exposed to the outside of the operating part 22 or a form where the slider housing space is formed inside a cap by mounting the cap (not illustrated), which blocks the slider housing space 150, on the opening part 23 of the operating part 22. Additionally, the cross-sectional shape of the slider housing space 150 in the direction orthogonal to the longitudinal axis A is not limited to the fan shape and may be, for example, a space, such as a rectangular shape or a circular shape.

Next, the slider 96 will be described.

The slider 96 is disposed in the slider housing space 150 and moves in the longitudinal direction of the operating part 22 depending on the operation of the erection operating lever 20 so as to be movable forward and backward. That is, in a case where the erection operating lever 20 is operated, the slider 96 moves via the erection operating mechanism 120. As a result, the wire 60 (refer to FIG. 2) coupled to the slider 96 is pushed and pulled.

As illustrated in FIG. 10, a protruding strip 97 along the longitudinal axis A is formed on a lower surface of the slider 96. Additionally, as illustrated in FIGS. 11 and 12, a recessed strip 99 along the longitudinal axis A is formed in an upper surface of the body part 98A of the base member 98. The slider 96 moves smoothly along the longitudinal axis A as the protruding strip 97 is slidably engaged with the recessed strip 99.

Next, an embodiment of a connection structure in which the proximal end side of the wire 60 is connected to the slider 96 will be described.

Figure 13:
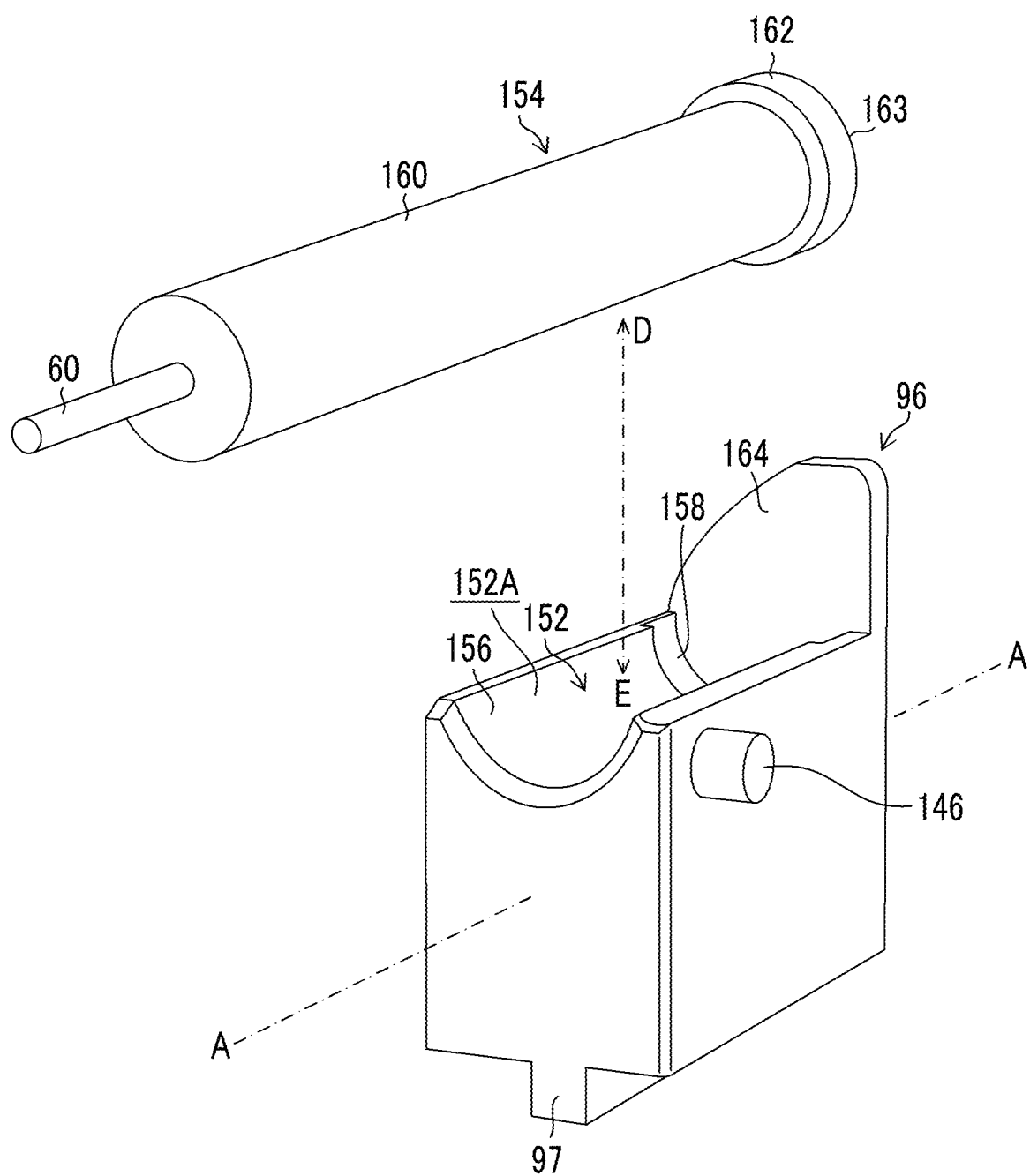
FIG. 13 is an assembling perspective view illustrating a connection structure between the slider and a proximal end side of a wire.

FIG. 13 is an assembling perspective view illustrating a connection structure of a first embodiment in which the proximal end side of the wire 60 is connected to the slider 96.

As illustrated in FIG. 13, the slider 96 is formed in a substantially cubical shape, and an engaged part 152 is provided in an upper surface in FIG. 13. The engaged part 152 is recessed in the upper surface of the slider 96 such that an opening part 152A of the engaged part 152 faces a lateral side (a direction of arrow D) orthogonal to a movement direction of the slider 96. In addition, the movement direction of the slider and the direction of the longitudinal axis A are the same directions.

Meanwhile, the engaging member 154 is provided on the proximal end side of the wire 60. The engaging member 154 is configured to be engageable with the engaged part 152 by being pushed into the engaged part 152 from the lateral side orthogonal to the movement direction of the slider 96. In addition, in FIG. 13, the push direction in which the engaging member 154 is pushed into the engaged part 152 is illustrated by arrow E.

The engaged part 152 has an engagement receiving part 156 that extends linearly in the movement direction of the slider 96, and a positioning receiving part 158 that is provided on a proximal end side of the engagement receiving part 156 and positions the engaging member 154 in the engaged part 152. The cross-sectional shapes of the engagement receiving part 156 and the positioning receiving part 158 in the direction orthogonal to the movement direction of the slider 96 are semicircular shapes, respectively, and the positioning receiving part 158 is formed in a semicircular shape having a larger diameter than the engagement receiving part 156.

The engaging member 154 has an engaging body part 160 engaging with the engagement receiving part 156, and a positioning part 162 engaging with the positioning receiving part 158. The engaging body part 160 is constituted of a columnar part, and the positioning part 162 is constituted of a disk-shaped head part formed to have a larger diameter than the columnar part. That is, the engaging member 154 has the columnar part that constitutes the engaging body part 160, and the head part that is formed to have a larger diameter than the columnar part and constitutes the positioning part 162.

The slider 96 and the engaging member 154 are made of elastically deformable rubber or plastic as an example, and the engaging body part 160 is engaged with the engagement receiving part 156 with elasticity by pushing the engaging body part 160 into the engagement receiving part 156 while being elastically deformed.

Additionally, the slider 96 has a guide surface 164 that guides the positioning part 162 to the positioning receiving part 158. The guide surface 164 is provided continuously with the positioning receiving part 158. The positioning part 162 is guided to the positioning receiving part 158 by causing a proximal-end-side end surface 163 of the positioning part 162 to abut against this guide surface 164.

Next, the connection work of connecting the proximal end side of the wire 60 to the slider 96 by the connection structure of the first embodiment will be described.

Before the proximal end side of the wire 60 is connected to the slider 96, the coupling work of coupling the distal end of the wire 60 to the elevator 30 is performed. In this coupling work, first, the wire 60 is introduced with the engaging member 100 as a head from the opening part 94 of FIG. 6 in a state (refer to FIG. 3) where the elevator 30 is located at the erected position. As a result, the engaging member 100 is delivered from the delivery port 74 to the outside via the wire channel 62 (refer to FIG. 2). Then, the engaging member 100 is guided toward the opening 104 of the housing groove 102 of the elevator 30 by the engagement guide part 106 of FIG. 3 by continuing the introduction operation of the wire 60 and is engaged with the housing groove 102 from the opening 104. Thus, the coupling work of coupling the distal end of the wire 60 to the elevator 30 is completed.

Next, the connection work of connecting the proximal end side of the wire 60 to the slider 96 is performed. In this connection work, first, the positioning part 162 and the positioning receiving part 158 are relatively positioned in a pushing direction (a direction of arrow E) by causing the proximal-end-side end surface 163 of the engaging member 154 illustrated in FIG. 13 to abut against the guide surface 164 of the slider 96. In this way, the positioning part 162 can be easily guided to the positioning receiving part 158 by providing the slider 96 with the guide surface 164.

Next, the engaging member 154 is pushed into the engaged part 152 in the direction of arrow E from the lateral side orthogonal to the movement direction of the slider 96. By this pushing work, the engaging body part 160 is engaged with the engagement receiving part 156 with elasticity. Thus, the above connection work is completed.

In this way, according to the connection structure of the first embodiment, the connection work of connecting the proximal end side of the wire 60 to the slider 96 can be performed simply by the work of pushing the engaging member 154 into the engaged part 152. As a result, according to the connection structure of the first embodiment, the proximal end side of the wire 60 can be easily connected to the slider 96.

Meanwhile, the endoscope 10 is used for various kinds of examination or treatment. Thereafter, the following work is carried out in a case where the endoscope 10 is cleaned.

First, the cap 76 illustrated in FIG. 2 is detached from the distal end member 28. Next, the proximal end side of the wire 60 is detached from the slider 96 of FIG. 6. This detachment work will be described below.

Next, the wire 60 is pushed from the opening part 94 illustrated in FIG. 6, and the elevator 30 is located at the lodged position of FIG. 2 from the erected position of FIG. 3. Thereafter, the wire 60 is further pushed so as to separate the engaging member 100 from the inside of the housing groove 102 to the outside of the opening 104. By this work, the distal end of the wire 60 is detached from the elevator 30. Next, the wire 60 is pulled out from the opening part 94 to the outside to empty the wire channel 62. Thereafter, the distal end member 28, the elevator 30, and the wire channel 62 are cleaned.

In the detachment work of detaching the proximal end side of the wire 60 from the slider 96, the connection structure of the first embodiment pulls out the engaging member 154 from the engaged part 152 to a direction (the direction of arrow D) opposite to the pushing direction (the direction of arrow E) of the engaging member 154 with respect to the engaged part 152 carried out at the time of the connection work. The detachment work is completed simply by this pulling-out work. Therefore, according to the connection structure of the first embodiment, the proximal end side of the wire 60 can be easily detached from the slider 96.

As described above, according to the connection structure of the first embodiment, the connection work of connecting the proximal end side of the wire 60 to the slider 96 can be performed simply by the work of pushing the engaging member 154 into the engaged part 152. Additionally, the detachment work of detaching the proximal end side of the wire 60 from the slider 96 can be performed simply by the work of pulling out the engaging member 154 from the engaged part 152.

Hence, according to the connection structure of the first embodiment, the attachment and detachment work of the proximal end of the wire 60 with respect to the slider 96 can be easily performed compared to the endoscope of JP1994-315458A (JP-H06-315458A) that performs the attachment and detachment work of the proximal end side of the wire with respect to the slider using the set screw, and the endoscope of EP1759626B in which the distal end of the cable cord is attachably and detachably mounted on the collet and the nut.

Additionally, since the connection structure of the first embodiment comprises the positioning receiving part 158 and the positioning part 162, the engagement between the engaged part 152 and the engaging member 154 becomes easy by engaging the positioning part 162 with the positioning receiving part 158. Additionally, by engaging the positioning part 162 with the positioning receiving part 158, the engaging member 154 can be prevented from slipping out from the engaged part 152 in the axial direction of the wire 60.

Additionally, the cross-sectional shapes of the engagement receiving part 156 and the positioning receiving part 158 are not limited to the semicircular shapes and may be rectangular shapes. Similarly, the engaging body part 160 may be formed in a prismatic shape s without being limited to the columnar shape, and the positioning part 162 may be formed in a rectangular shape without being limited to being a disk shape.

Additionally, since the slider 96 has the guide surface 164, the positioning part 162 can be easily guided to the positioning receiving part 158 simply by pressing the proximal-end-side end surface 163 of the positioning part 162 against the guide surface 164.

Additionally, in the connection structure of the first embodiment, a form in which the engaged part 152 is recessed in the slider 96 has been exemplified. However, the engaged part 152 may be formed in a form protruding from the slider 96. In this case, the engaging member 154, which is engageable with the engaged part 152, has a form comprising a recess engaged with a protrusion of the engaged part 152.

Additionally, in the connection structure of the first embodiment, an example in which the positioning receiving part 158 is provided on the proximal end side of the engagement receiving part 156 has been described. However, the invention is not limited to this. That is, the positioning receiving part 158 may be provided on the distal end side of the engagement receiving part 156. That is, the positioning receiving part 158 may be provided in the engagement receiving part 156.

Additionally, in the connection structure of the first embodiment, a form in which the slider 96 moves forward and backward in the direction parallel to the longitudinal axis A is provided. However, the movement direction of the slider of the invention is not limited to the direction parallel to the longitudinal direction. That is, the movement direction of the slider of the invention also includes a form in which the slider moves forward and backward in a direction inclined with respect to the longitudinal direction. That is, a form in which the slider moves forward and backward in a direction having a component of the longitudinal direction is included. This form is described in the following respective embodiments.

Next, a connection structure of a second embodiment in which the proximal end side of the wire 60 is connected to the slider will be described.

In addition, in describing the connection structure of the second embodiment, the same or similar members as those of the connection structure of the first embodiment described in FIG. 13 will be designated by the same reference signs and described.

Figure 14:
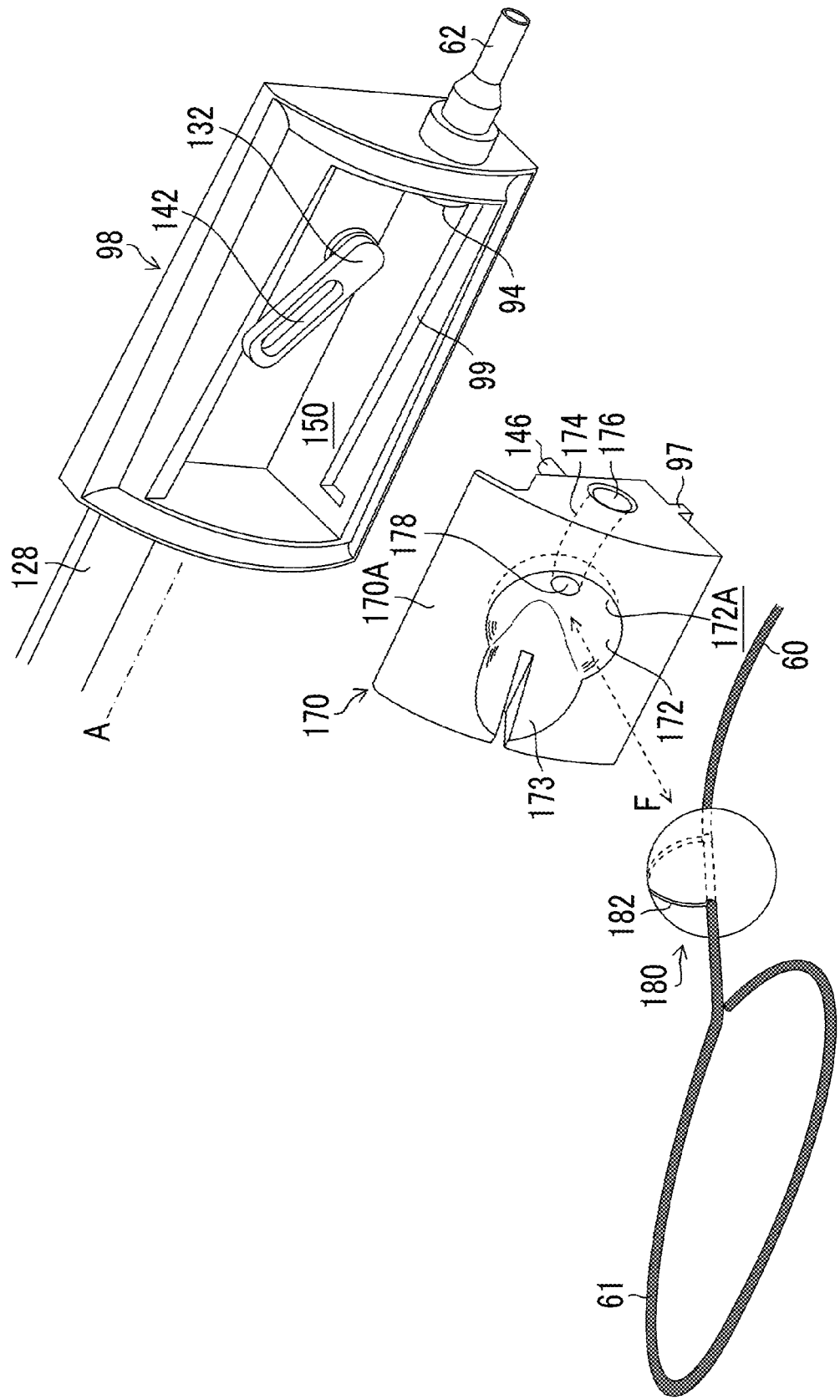
FIG. 14 is an assembling perspective view illustrating constituent members of a connection structure of a second embodiment.

FIG. 14 is an assembling perspective view illustrating constituent members of the connection structure of the second embodiment. A state before the proximal end side of the wire 60 is connected to a slider 170 is illustrated in FIG. 14. Additionally, a state where the proximal end side of the wire 60 is connected to the slider 170 is illustrated in FIG. 15.

As illustrated in FIG. 14, the slider 170 comprises the cam pin 146 engaging with the cam groove 142 of the second lever 132, and the protruding strip 97 engaging with the recessed strip 99 of the base member 98. Similarly to the slider 96 illustrated in FIGS. 11 and 12, the slider 170 is also disposed in the slider housing space 150 and moves forward and backward in the longitudinal direction along the longitudinal axis A of the operating part 22 depending on the operation of the erection operating lever 20 (refer to FIG. 9).

As illustrated in FIG. 14, an engaged part 172 is formed on a front surface 170A of the slider 170. The engaged part 172 is recessed in the front surface 170A of the slider 170 such that an opening part 172A of the engaged part 172 faces a lateral side (a direction of arrow F) orthogonal to a movement direction of the slider 170. The engaged part 172 is formed in a hemispherical shape. Additionally, a wire insertion passage 174 is formed in the slider 170. As illustrated in FIG. 15, the wire insertion passage 174 is a passage that allows an opening part 176 disposed at a position facing the opening part 94 of the wire channel 62 and an opening part 178 (to refer to FIG. 14) formed in the engaged part 172 to communicate with each other, and is formed inside the slider 170. In a case where the distal end of the wire 60 is coupled to the elevator 30 (refer to FIG. 3), the wire 60 is inserted into the wire insertion passage 174 from the opening part 178 and is inserted into the opening part 94 from the opening part 176.

The engaging member 180, which is engageable with the engaged part 172, is formed as a spherical body. The engaging member 180 is pushed into the engaged part 172 in a direction of arrow G of FIG. 14 from the lateral side orthogonal to the movement direction of the slider 170. As a result, the engaging member 180 is engaged with the engaged part 172 with elasticity.

The engaging member 180 has a slit-shaped sandwiching part 182 into which the proximal end side of the wire 60 is inserted from the outer surface side of the engaging member 180 to perform sandwiching. The sandwiching part 182 is constituted of a semicircular slit formed inward from an outer surface of the engaging member 180.

Figure 16A:
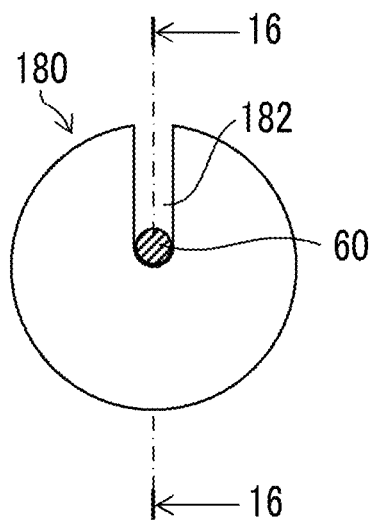
FIG. 16A is an explanatory view illustrating a state where the wire is sandwiched by a sandwiching part of an engaging member.
Figure 16B:
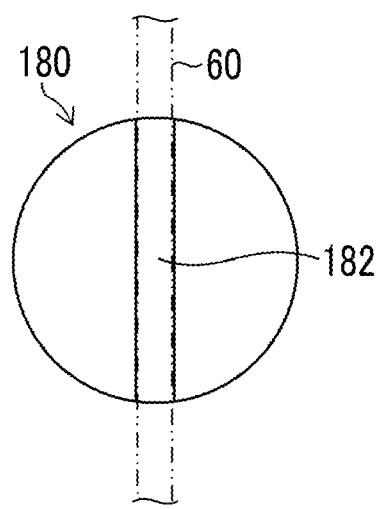
FIG. 16B is a top view of FIG. 16A.
Figure 16C:
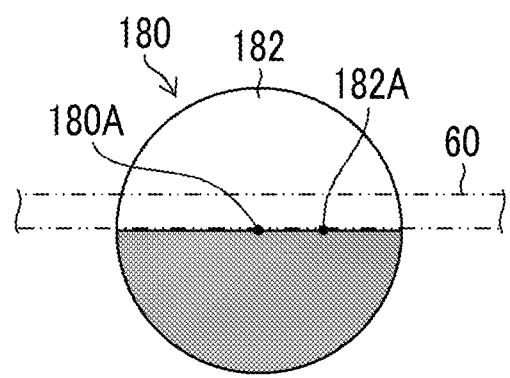
FIG. 16C is a cross-sectional view of the engaging member taken along line 16-16 of FIG. 16A.
Figure 16D:
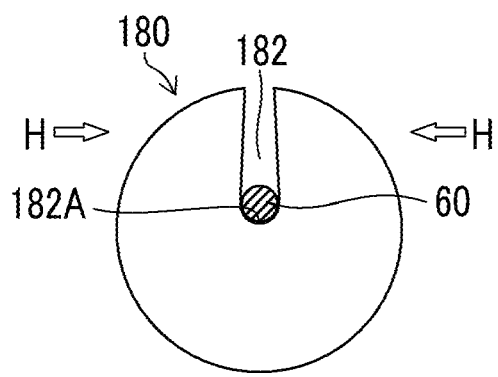
FIG. 16D is an explanatory view illustrating the state of the sandwiching part in a case where the engaging member is engaged with an engaged part.

FIG. 16A is a front view of the engaging member 180 illustrating a state where the proximal end side of the wire 60 is inserted into the sandwiching part 182 of the engaging member 180. FIG. 16B is a top view of FIG. 16A. FIG. 16C is a cross-sectional view of the engaging member 180 taken along line 16-16 of FIG. 16A. Additionally, FIG. 16D is an explanatory view illustrating the state of the sandwiching part 182 in a case where the engaging member 180 is engaged with the engaged part 172.

As illustrated in FIG. 16A, the proximal end side of the wire 60 is inserted into the sandwiching part 182 of the engaging member 180. As illustrated in FIG. 16C, a bottom surface 182A of a slit, which is the sandwiching part 182, reaches a center 180A of the engaging member 180. As a result, the proximal end side of the wire 60 is sandwiched at the center 180A of the engaging member 180.

Next, the connection work of connecting the proximal end side of the wire 60 to the slider 96 by the connection structure of the second embodiment will be described.

First, the proximal end side of the wire 60 is inserted into the sandwiching part 182 of the engaging member 180. In this state, the distal end of the wire 60 is inserted through the wire channel 62 via the wire insertion passage 174, the opening part 176, and the opening part 94 from the opening part 178 of the slider 170. Then, the distal end of the wire 60 is coupled to the elevator 30 (refer to FIG. 3).

Next, the erection operating lever 20 (refer to FIG. 9) is operated to locate the slider 170 at the erected position of FIG. 15.

Thereafter, a finger is hooked on a loop part 61 formed on the proximal end side of the wire 60 to pull the wire 60 in a pulling direction and loosen the wire 60. In this state, the engaging member 180 is pushed into the engaged part 172 in the direction of arrow G (refer to FIG. 14) from the lateral side orthogonal to the movement direction of the slider 170. By this pushing work, the engaging member 180 is engaged with the engaged part 172 with elasticity. In a case where the engaging member 180 is engaged with the engaged part 172, as illustrated in FIG. 16D, the engaging member 180 receives forces in the directions of arrows H from the engaged part 172 and is elastically deformed in a direction in which a gap of the sandwiching part 182 becomes narrower. As a result, the proximal end side of the wire 60 is firmly sandwiched by the sandwiching part 182 and is fixed to the engaging member 180. Thus, the above connection work is completed.

In this way, according to the connection structure of the second embodiment, the connection work of connecting the proximal end side of the wire 60 to the slider 170 can be performed simply by the work of pushing the engaging member 180 into the engaged part 172. As a result, according to the connection structure of the second embodiment, the proximal end side of the wire 60 can be easily connected to the slider 170.

On the other hand, in the detachment work of detaching the proximal end side of the wire 60 from the slider 170, the engaging member 180 is pulled out from the engaged part 172 to a direction (a direction of arrow F) opposite to the pushing direction (a direction of arrow G) of the engaging member 180 with respect to the engaged part 172 carried out at the time of the connection work. The detachment work is completed simply by this pulling-out work. Therefore, according to the connection structure of the second embodiment, the proximal end side of the wire 60 can be easily detached from the slider 170.

As described above, according to the connection structure of the second embodiment, the connection work of connecting the proximal end side of the wire 60 to the slider 170 can be performed simply by the work of pushing the engaging member 180 into the engaged part 172. Additionally, the detachment work of detaching the proximal end side of the wire 60 from the slider 170 can be performed simply by the work of pulling out the engaging member 180 from the engaged part 172.

Hence, according to the connection structure of the second embodiment, the attachment and detachment work of the proximal end side of the wire 60 with respect to the slider 170 can be easily performed similarly to the connection structure of the above-described first embodiment.

Additionally, according to the connection structure of the second embodiment, as illustrated in FIG. 16C, the bottom surface 182A of the sandwiching part 182 is made to reach the center 180A of the engaging member 180. As a result, according to the engaging member 180, the sandwiching force of the wire 60 by the sandwiching part 182 can be obtained to the maximum extent while the strength of the engaging member 180 is maintained. In addition, the bottom surface 182A of the sandwiching part 182 may reach the center 180A, and thus, the bottom surface 182A may reach a deep position from the center 180A.

In addition, at the time of the detachment work, the engaging member 180 is pulled out from the engaged part 172 by hooking a finger on the loop part 61 of the wire 60 to pull the wire 60. As a result, the pulling of the wire 60 can be easily performed.

Figure 17:
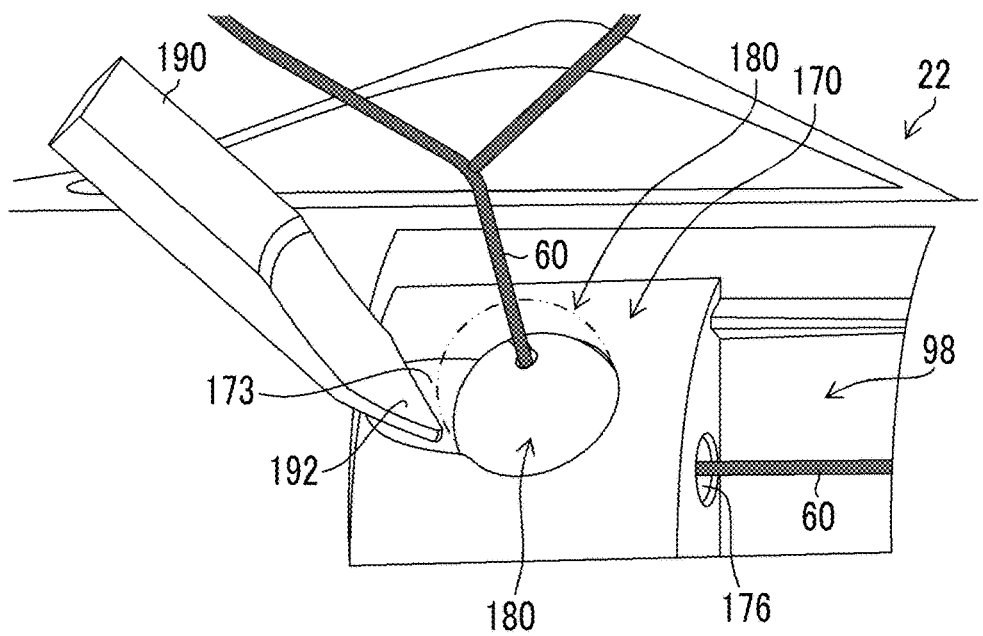
FIG. 17 is an explanatory view in which the engaging member is detached from the engaged part using a jig.

Additionally, a jig can also be used to detach the engaging member 180 from the engaged part 172. FIG. 17 is an explanatory view illustrating a state where the engaging member 180 is detached from the engaged part 172 using the jig 190.

According to FIG. 17, an acute part 192 of a distal end of the jig 190 is inserted into a boundary part between the engaging member 180 and the engaged part 172, and the engaging member 180 is detached from the engaged part 172 according to the principle of the lever. In a case where the jig 190 is used in this way, the engaging member 180 can be easily detached from the engaged part 172. In this case, s concave guide surface 173 for guiding the acute part 192 of the jig 190 to the above boundary part may be provided continuously with the engaged part 172.

Figure 18:
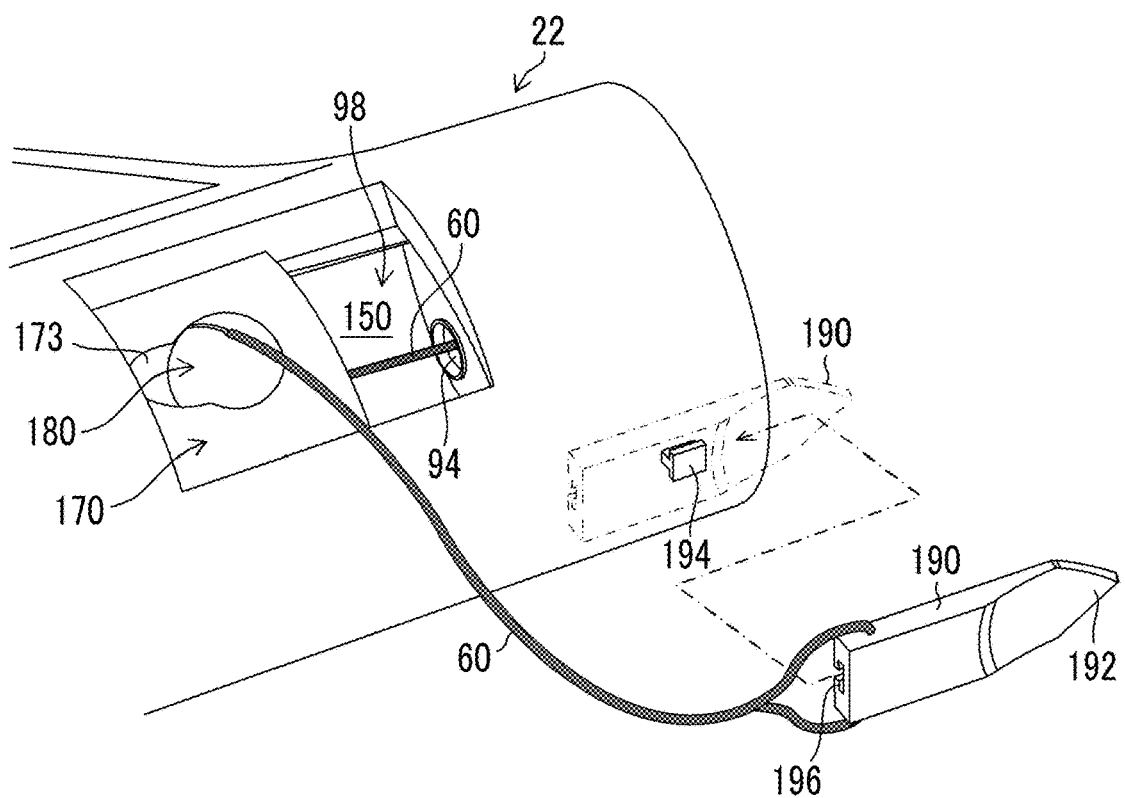
FIG. 18 is an explanatory view in which the jig is attached to a distal end side of the wire.

Additionally, as illustrated in FIG. 18, the jig 190 may be attached to the proximal end side of the wire 60. FIG. 18 is an explanatory view in which the jig 190 is attached to the proximal end side of the wire 60. Additionally, as illustrated in FIG. 18, a projection 194 holding the jig 190 may be provided in the operating part 22. The jig 190 is held by the operating part 22 by engaging a recess 196 formed in the jig 190 with the projection 194. As a result, since sagging of the jig 190 can be prevented, the jig 190 can be prevented from becoming obstructive during the operation of the endoscope 10 (refer to FIG. 1).

Next, a connection structure of a third embodiment in which the proximal end side of the wire 60 is connected to the slider will be described.

In addition, in describing the connection structure of the third embodiment, the same or similar members as those of the connection structure of the second embodiment described in FIGS. 14 to 18 will be designated by the same reference signs and described.

Figure 19:
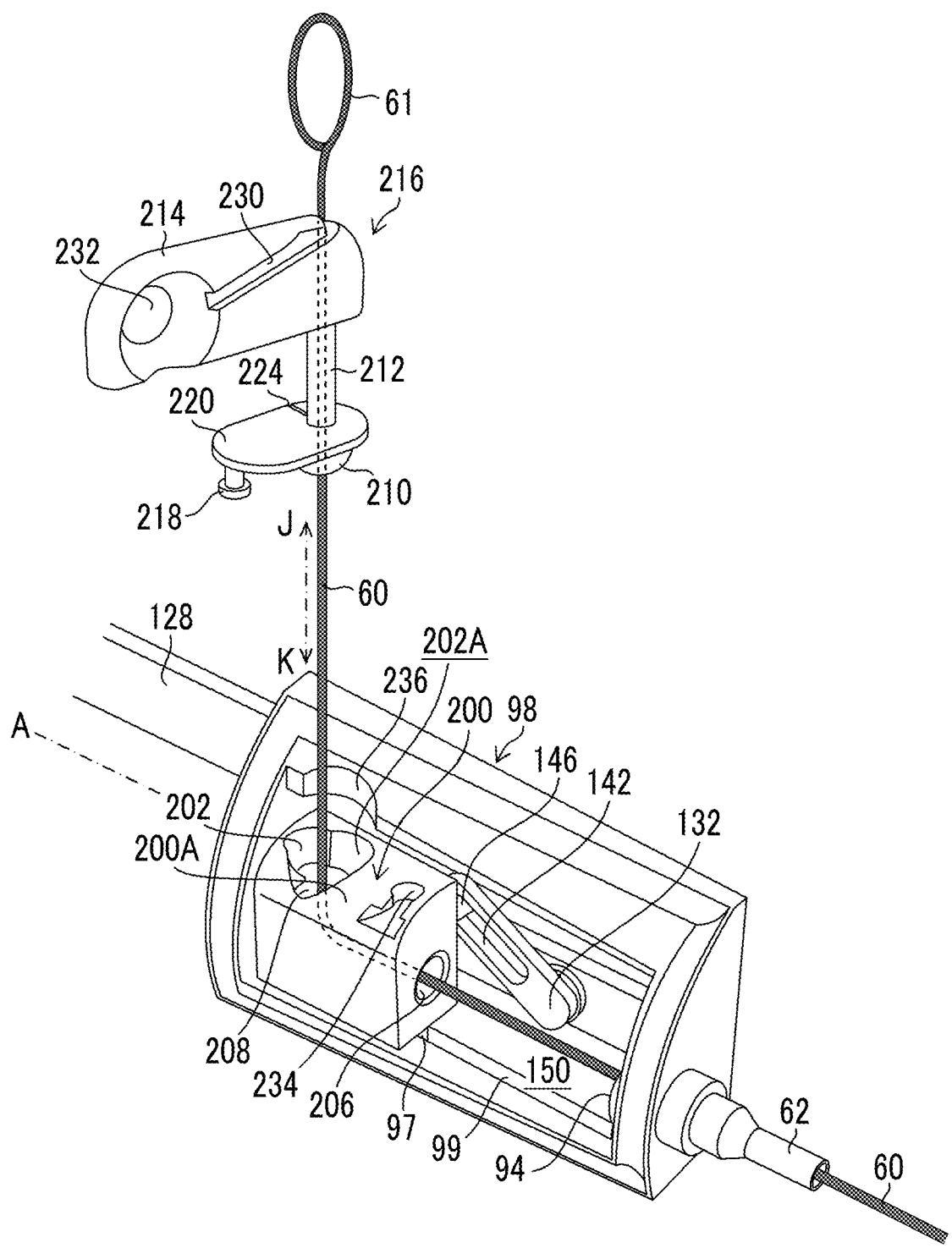
FIG. 19 is an assembling perspective view illustrating constituent members of a connection structure of a third embodiment.
Figure 20:
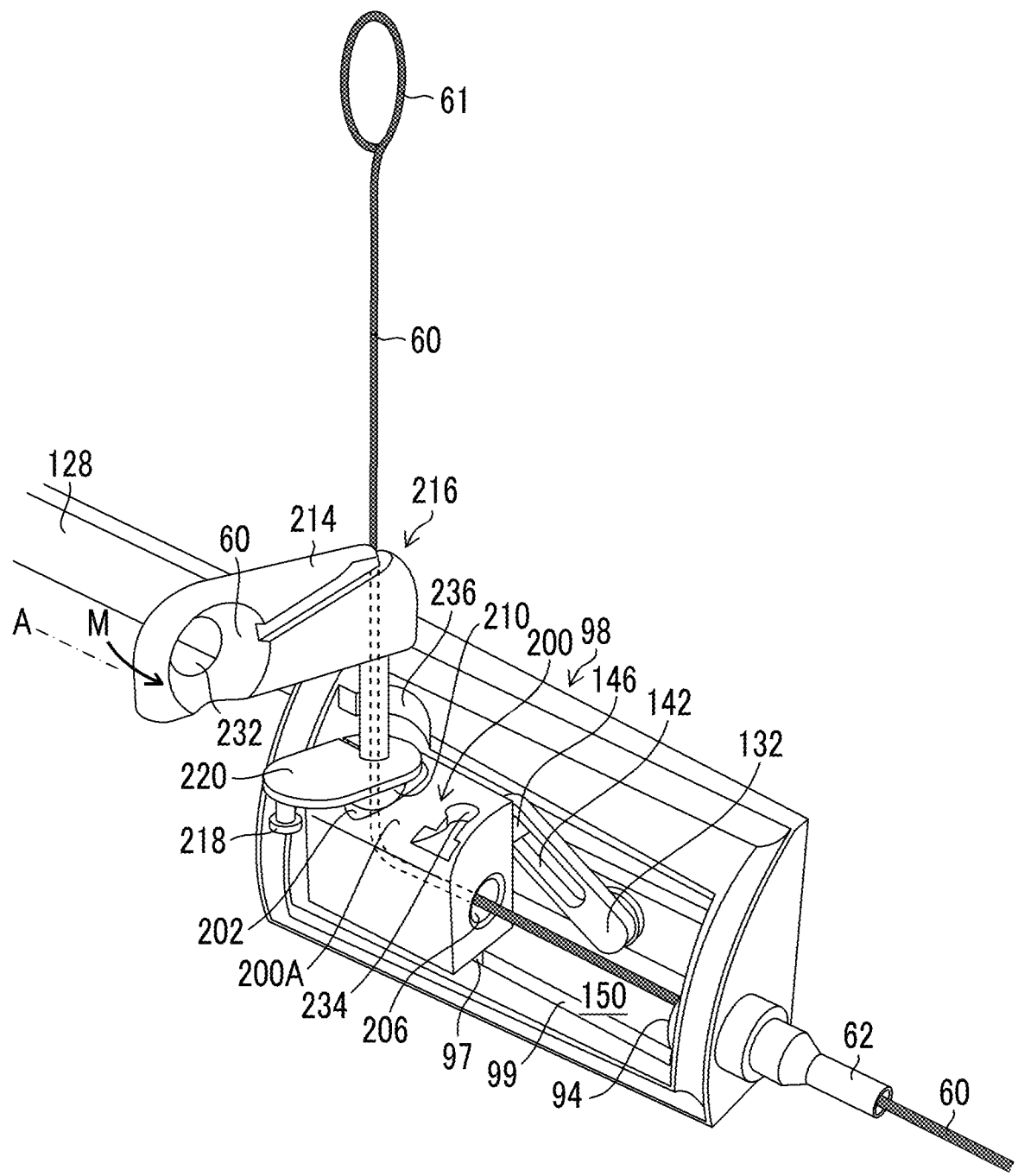
FIG. 20 is an explanatory view illustrating the state of an unlocked position in the connection structure of FIG. 19.

FIG. 19 is an assembling perspective view illustrating constituent members of the connection structure of the third embodiment. A state before the proximal end side of the wire 60 is connected to a slider 200 is illustrated in FIG. 19. Additionally, the state of an unlocked position in the connection structure of the third embodiment is illustrated in FIG. 20. Moreover, the state of a locked position in the connection structure of the third embodiment is illustrated in FIG. 21.

Figure 21:
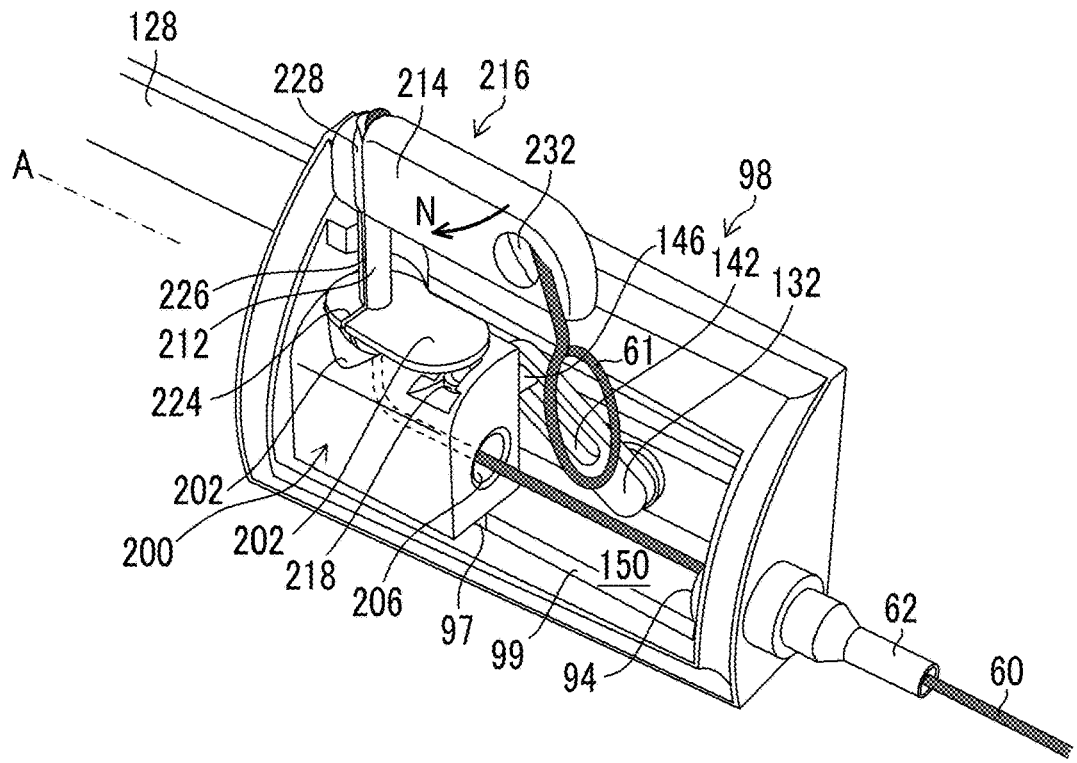
FIG. 21 is an explanatory view illustrating the state of a locked position in the connection structure of FIG. 19.

As illustrated in FIGS. 19 to 21, the slider 200 comprises the cam pin 146 engaging with the cam groove 142 of the second lever 132, and the protruding strip 97 engaging with the recessed strip 99 of the base member 98. Similarly to the slider 170 illustrated in FIG. 14, the slider 200 is disposed in the slider housing space 150 and moves forward and backward in the longitudinal direction along the longitudinal axis A of the operating part 22 depending on the operation of the erection operating lever 20 (refer to FIG. 9).

Figure 22:
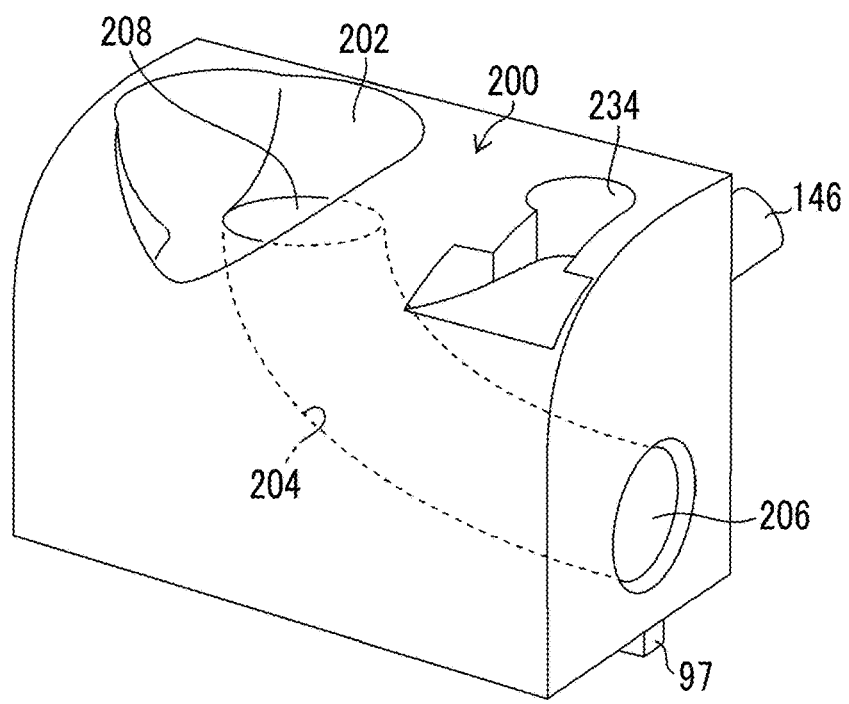
FIG. 22 is an enlarged perspective view illustrating the structure of the slider.

As illustrated in FIG. 19, an engaged part 202 is formed on a front surface 200A of the slider 200. The engaged part 202 is recessed in the front surface 200A of the slider 200 such that an opening part 202A of the engaged part 202 faces a lateral side (a direction of arrow J) orthogonal to a movement direction of the slider 200. The engaged part 202 is formed in a hemispherical shape. Additionally, as illustrated in FIG. 22, a wire insertion passage 204 is formed in the slider 200. FIG. 22 is an enlarged perspective view illustrating the structure of the slider 200.

The wire insertion passage 204 is a passage that allows an opening part 206 disposed at a position facing the opening part 94 (refer to FIG. 19) of the wire channel 62 and an opening part 208 formed in the engaged part 202 to communicate with each other, and is formed inside the slider 200. In a case where the distal end of the wire 60 is coupled to the elevator 30 (refer to FIG. 3), the wire 60 is inserted into the wire insertion passage 204 from the opening part 208 and is inserted into the opening part 94 (refer to FIG. 19) from the opening part 206.

As illustrated in FIG. 19, the engaging member 210, which is engageable with the engaged part 202, is formed as a hemisphere. The engaging member 210 is pushed into the engaged part 202 in a direction of arrow K of FIG. 19 from the lateral side orthogonal to the movement direction of the slider 200. As a result, the engaging member 210 is engaged with the engaged part 202 with elasticity.

The engaging member 210 is provided in a locking operating member 216 having a rotating shaft 212 and a knob 214. According to this locking operating member 216, in FIG. 19, the engaging member 210 is coupled to a lower end part of the rotating shaft 212, and the knob 214 is coupled to an upper end part of the rotating shaft 212. Additionally, the engaging member 210 and the rotating shaft 212 are coupled to each other such that respective central axes thereof are coaxially located.

Additionally, the locking operating member 216 has a locking member 218 to be described below, and the locking member 218 is coupled to the rotating shaft 212 via a bracket 220. That is, the locking member 218 is provided at a position offset from the central axis of the rotating shaft 212.

Figure 23:
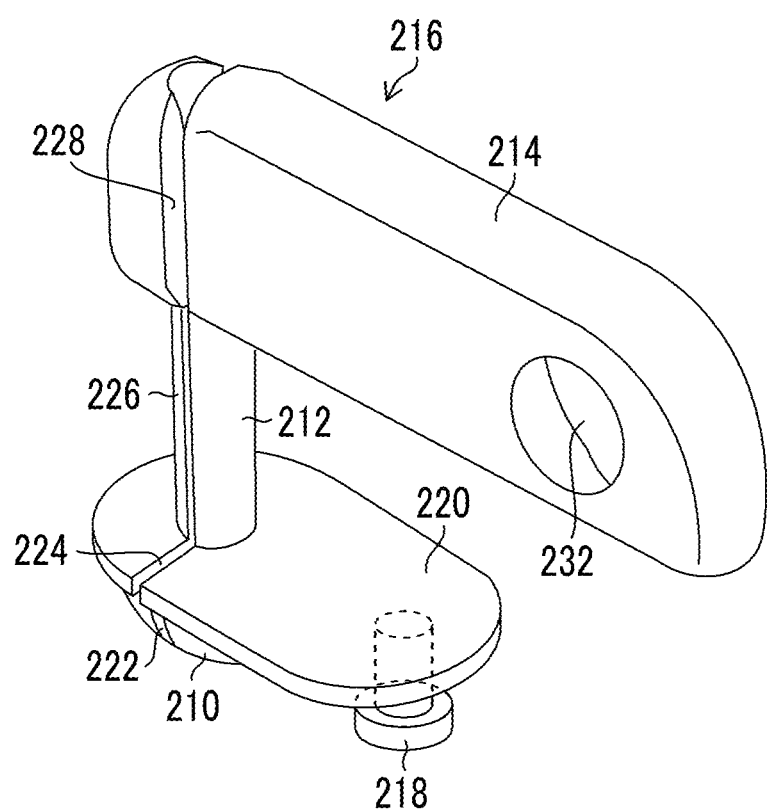
FIG. 23 is an enlarged perspective view illustrating the structure of a locking operating member.
Figure 24:
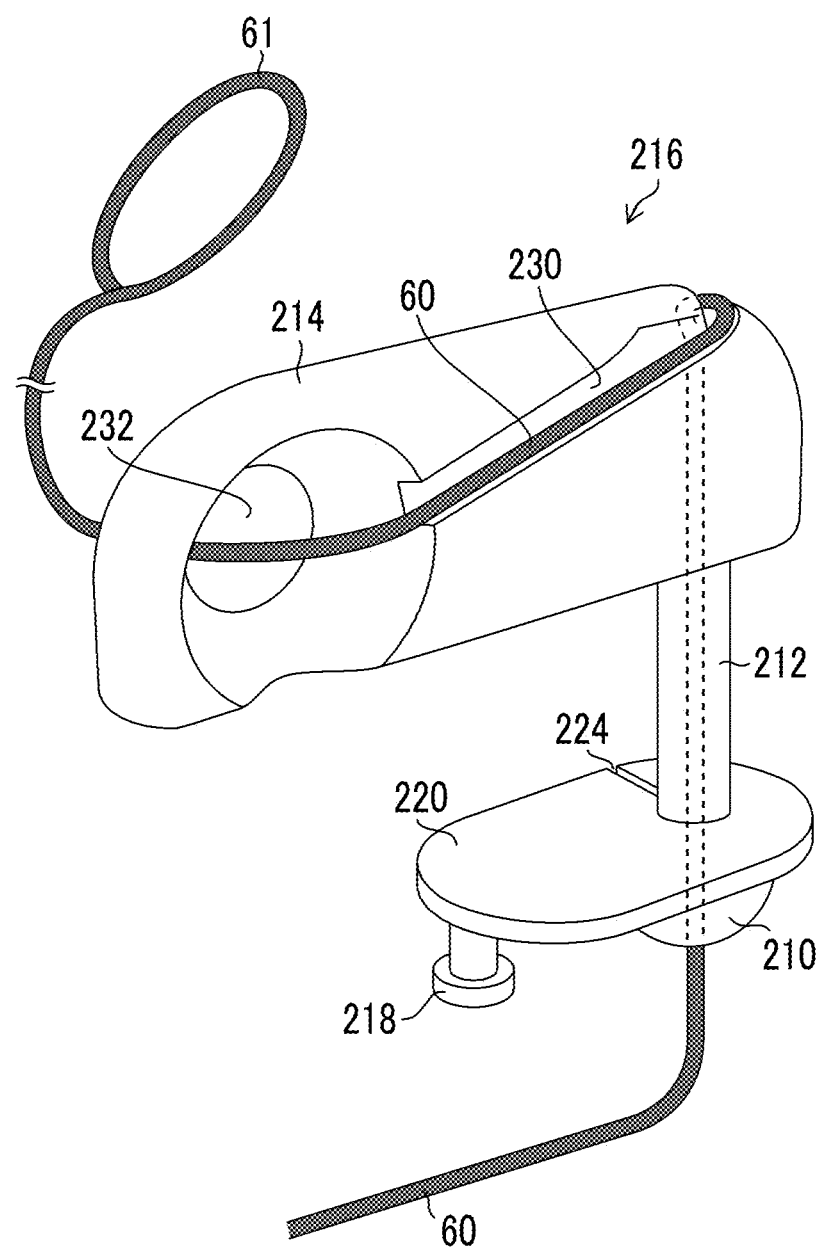
FIG. 24 is an enlarged perspective view in which the distal end side of the wire is locked to the locking operating member.
Figure 25:
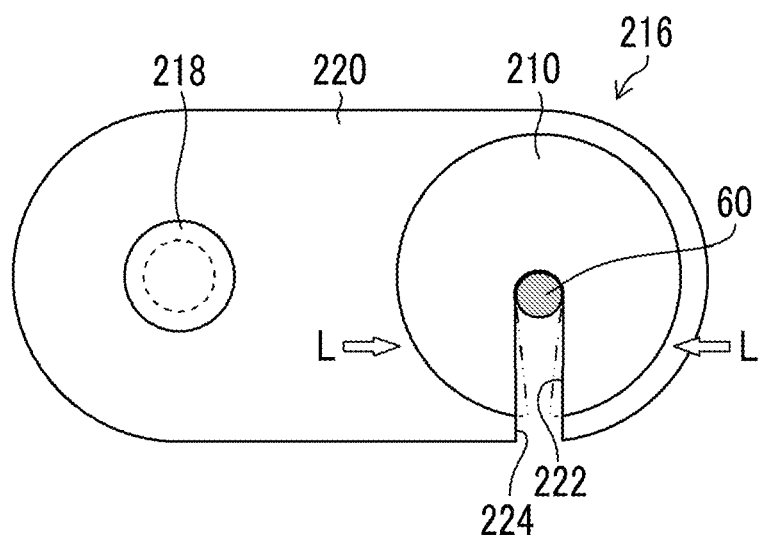
FIG. 25 is a bottom view of the locking operating member illustrated in FIG. 24.

FIG. 23 is an enlarged perspective view illustrating the structure of the locking operating member 216. FIG. 24 is an enlarged perspective view in which the proximal end side of the wire 60 is locked to the locking operating member 216. FIG. 25 is a bottom view of the locking operating member 216 illustrated in FIG. 24.

As illustrated in FIGS. 23 and 25, the engaging member 210 has a slit-shaped sandwiching part 222 in which the proximal end side of the wire 60 is inserted and sandwiched from the outer surface side of the engaging member 210. Additionally, a slit 224 for guiding the wire 60 to the sandwiching part 222 is formed in the bracket 220, and similarly, slits 226 and 228 are also formed in the rotating shaft 212 and the knob 214. The proximal end side of the wire 60 is inserted into the sandwiching part 222 of the engaging member 210 via the slits 224, 226, and 228. Additionally, as illustrated in FIG. 24, the proximal end side of the wire 60 is disposed along a groove 230 formed in the knob 214, and the loop part 61 of the wire 60 is inserted into an opening part 232 of the knob 214. As a result, the proximal end side of the wire 60 is locked to an inner peripheral part of the opening part 232.

Additionally, the connection structure of the third embodiment comprises a locking mechanism. This locking mechanism is switchable between the locked position (refer to FIG. 21) where release of an engaged state between the engaging member 210 and the engaged part 202 is prevented and the unlocked position (refer to FIG. 20) where the release of the engaged state between the engaging member 210 and the engaged part 202 is allowed.

The locking mechanism is configured to comprise the locking member 218 provided adjacent to the engaging member 210, and a locking recess 234 (refer to FIG. 22) that is provided in the slider 200 and engages with the locking member 218. According to the locking mechanism, the locked position (refer to FIG. 21) is reached in a case where the locking member 218 and the locking recess 234 are engaged with each other, and the unlocked position (refer to FIG. 20) is reached in a case where the engagement between the locking member 218 and the locking recess 234 is released.

Next, the connection work of connecting the proximal end side of the wire 60 to the slider 200 by the connection structure of the third embodiment will be described.

First, the proximal end side of the wire 60 is inserted into the sandwiching part 222 of the engaging member 210. In this state, the distal end of the wire 60 is inserted through the wire channel 62 via the wire insertion passage 204, the opening part 206, and the opening part 94 (refer to FIG. 19) from the opening part 208 (refer to FIG. 22) of the slider 200. Then, the distal end of the wire 60 is coupled to the elevator 30 (refer to FIG. 3).

Next, the erection operating lever 20 (refer to FIG. 9) is operated to locate the slider 200 at the erected position of FIG. 19.

Thereafter, a finger is hooked on the loop part 61 of the wire 60 to pull the wire 60 in the pulling direction and loosen the wire 60. In this state, the engaging member 210 is pushed into the engaged part 202 in a direction of arrow K from the lateral side orthogonal to the movement direction of the slider 200. By this pushing work, the engaging member 210 is engaged with the engaged part 202 with elasticity. As illustrated in FIG. 20, in a case where the engaging member 210 is engaged with the engaged part 202, as illustrated in FIG. 25, the engaging member 210 receives forces in the directions of arrows L from the engaged part 202 and is elastically deformed in a direction in which a gap of the sandwiching part 222 becomes narrower. As a result, the proximal end side of the wire 60 is firmly sandwiched by the sandwiching part 222 and is fixed to the engaging member 210.

Next, in a case where the locking operating member 216 in the state of the unlocked position of FIG. 20 is rotated 90 degrees in a direction of arrow M using the knob 214, as illustrated in FIG. 21, the locking member 218 is engaged with the locking recess 234 of the slider 200 and reaches the locked position. As a result, the slip-out of the engaging member 210 in the direction of arrow J with respect to the engaged part 202 can be prevented. Then, as illustrated in FIG. 21, the loop part 61 of the wire 60 is inserted into the opening part 232 and the proximal end side of the wire 60 is locked to the inner peripheral part of the opening part 232 such that a procedure is not affected. Thus, the above connection work is completed.

In this way, according to the connection structure of the third embodiment, the connection work of connecting the proximal end side of the wire 60 to the slider 200 can be performed simply by the work of pushing the engaging member 210 into the engaged part 202 and the work of engaging the locking member 218 with the locking recess 234. As a result, according to the connection structure of the third embodiment, the proximal end side of the wire 60 can be easily connected to the slider 200.

On the other hand, in a case where the proximal end side of the wire 60 is detached from the slider 200, first, the locking operating member 216 in the state of the locked position of FIG. 21 is rotated 90 degrees in a direction of arrow N using the knob 214. As a result, as illustrated in FIG. 20, the locking member 218 is separated from the locking recess 234 of the slider 200 and reaches the unlocked position. Next, the engaging member 210 is pulled out from the engaged part 202 in the direction (the direction of arrow J: refer to FIG. 19) opposite to the pushing direction (the direction of arrow K: refer to FIG. 19) of the engaging member 210 with respect to the engaged part 202. The detachment work is completed simply by this work. Therefore, according to the connection structure of the third embodiment, the proximal end side of the wire 60 can be easily detached from the slider 200.

As described above, according to the connection structure of the third embodiment, the connection work of connecting the proximal end side of the wire 60 to the slider 200 can be performed simply by the work of pushing the engaging member 210 into the engaged part 202 and the work of engaging the locking member 218 with the locking recess 234. Additionally, the detachment work of detaching the proximal end side of the wire 60 from the slider 200 can be performed simply by the work of detaching the locking member 218 from the locking recess 234 and the work of pulling out the engaging member 210 from the engaged part 202. Additionally, according to the connection structure of the third embodiment, the connection work of connecting the proximal end side of the wire 60 to the slider 200 can also be performed simply by the work of pushing the engaging member 210 into the engaged part 202. Additionally, according to the connection structure of the third embodiment, the proximal end side of the wire 60 can also be detached from the slider 200 simply by the work of pulling the engaging member 210 from the engaged part 202.

Hence, according to the connection structure of the third embodiment, the attachment and detachment work of the proximal end side of the wire 60 with respect to the slider 200 can be easily performed similarly to the connection structures of the above-described respective embodiments.

In addition, according to the connection structure of the third embodiment, the locking recess 234 is provided in the slider 200, and the locking member 218 is provided on the engaging member 210 side. However, the locking member 218 may be provided in the slider 200, and the locking recess 234 may be provided on the engaging member 210 side.

Additionally, as illustrated in FIG. 19, in a case where the engaging member 210 is pushed in the direction of arrow K, there is a case where the bracket 220 interferes with the base member 98. In this case, it is preferable to form a concave escape part 236 for allowing the pushing movement of the bracket 220 in the base member 98. As a result, the interference of the bracket 220 with the base member 98 in a case where the bracket 220 is moved to be pushed to the base member 98 can be prevented.

Additionally, there are the following advantages by providing the escape part 236. That is, the engaging member 210 cannot engage with the engaged part 202 only in a case where the slider 200 is located at the position of FIG. 19, that is, and the slider 200 is located at the erected position. In contrast, in a case where the engaging member 210 is engaged with the engaged part 202 at positions other than the position of FIG. 19 in a state where the elevator 30 is connected to the wire 60 in an erected state (refer to FIG. 3), there is a concern that the operation of the slider 200 is impossible. By providing the escape part 236 in this way, the engaging member 210 can engage with the engaged part 202 only at the position of FIG. 19. Thus, the problem that the operation of the slider 200 becomes impossible can be solved.

In addition, in a case where the engaged part 202 is engaged with the engaging member 210 in a state where the elevator 30 is connected to the wire 60 in a lodged state (refer to FIG. 2), the escape part 236 may be formed at a position corresponding to the lodged position of the slider 200.

Next, a connection structure of a fourth embodiment in which the proximal end side of the wire 60 is connected to the slider will be described.

In addition, in describing the connection structure of the fourth embodiment, the same or similar members as those of the connection structure of the third embodiment described in FIGS. 19 to 25 will be designated by the same reference signs and described.

Figure 26:
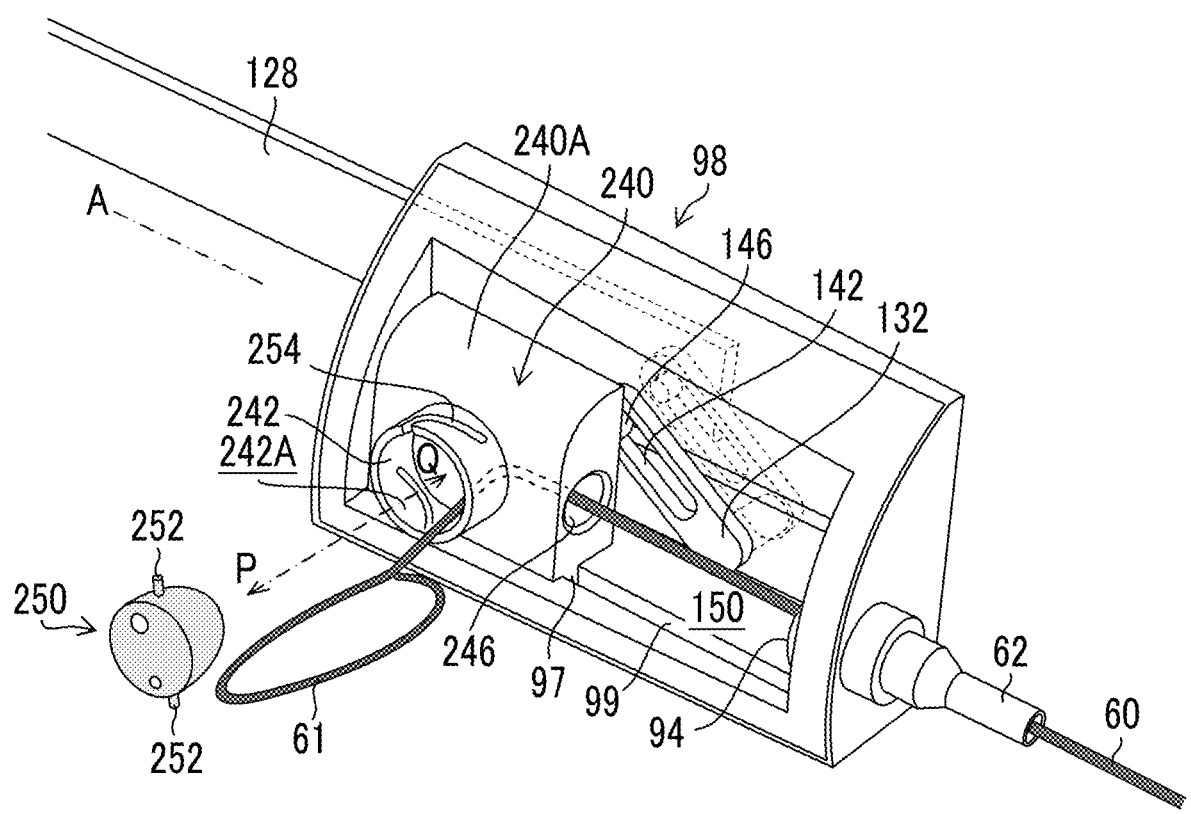
FIG. 26 is an assembling perspective view illustrating constituent members of a connection structure of a fourth embodiment.
Figure 27:
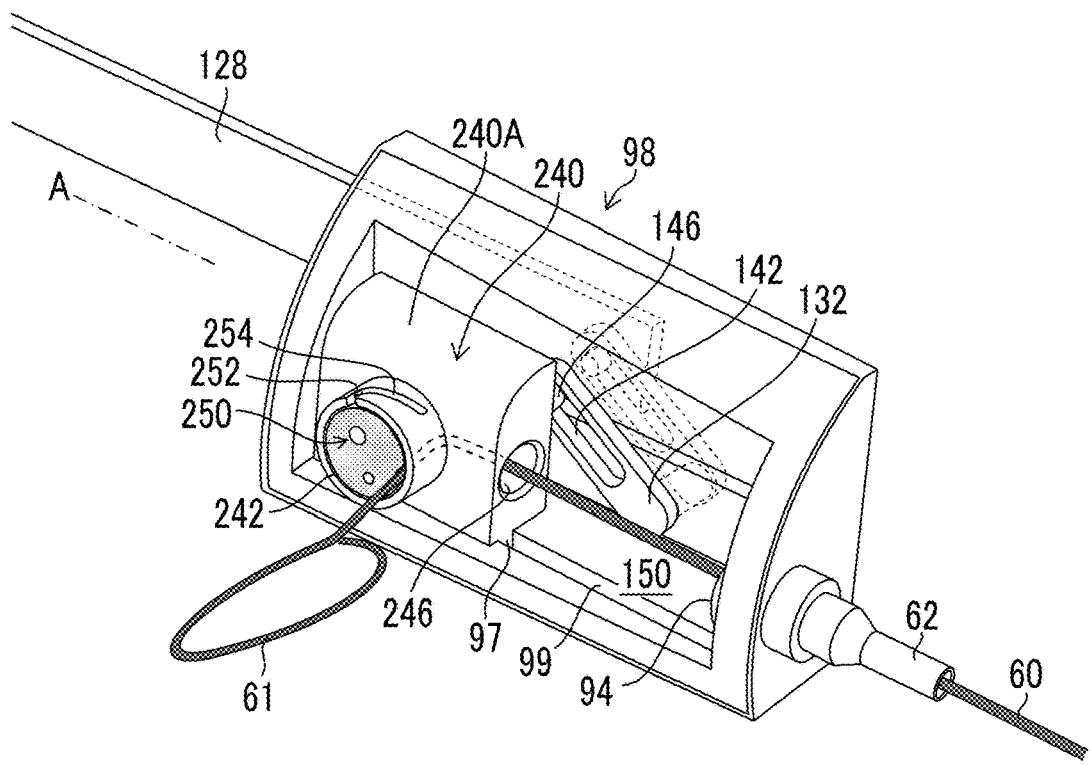
FIG. 27 is an explanatory view illustrating the state of the unlocked position in the connection structure of FIG. 26.

FIG. 26 is an assembling perspective view illustrating constituent members of the connection structure of the fourth embodiment. A state before the proximal end side of the wire 60 is connected to a slider 240 is illustrated in FIG. 26. Additionally, the state of an unlocked position in the connection structure of the fourth embodiment is illustrated in FIG. 27. Moreover, the state of a locked position in the connection structure of the fourth embodiment is illustrated in FIG. 28.

Figure 28:
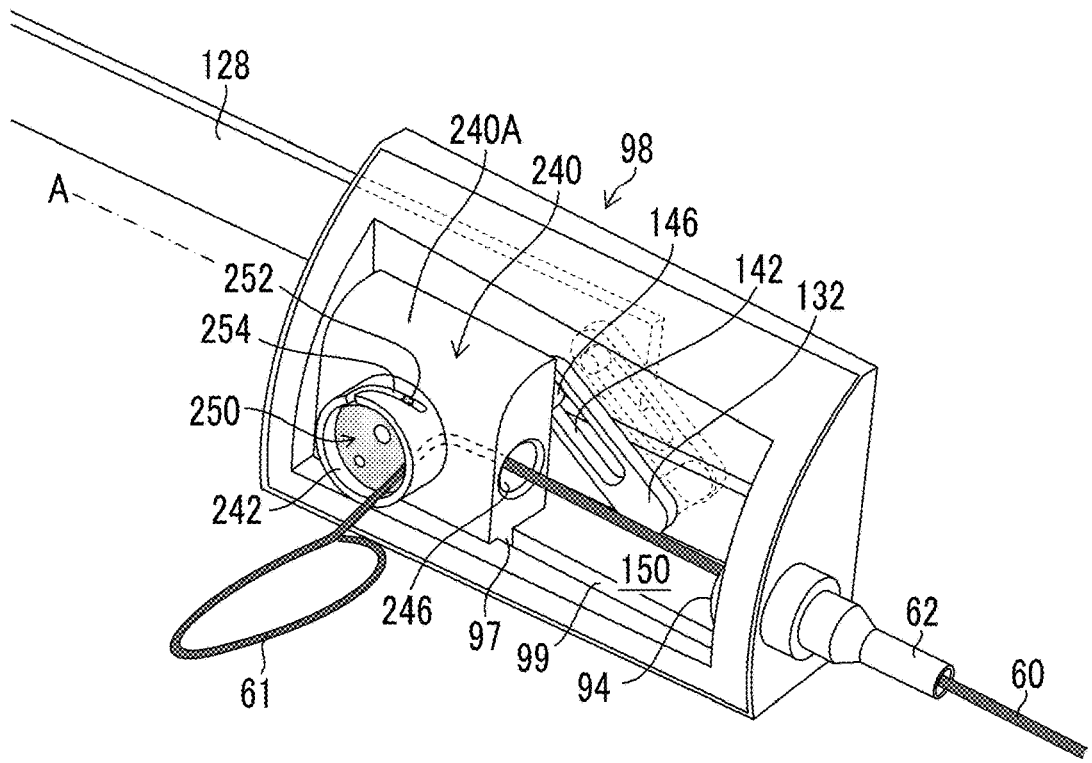
FIG. 28 is an explanatory view illustrating the state of the locked position in the connection structure of FIG. 26.

As illustrated in FIGS. 26 to 28, the slider 240 comprises the cam pin 146 engaging with the cam groove 142 of the second lever 132, and the protruding strip 97 engaging with the recessed strip 99 of the base member 98. Similarly to the slider 200 illustrated in FIG. 19, the slider 240 is disposed in the slider housing space 150 and moves forward and backward in the longitudinal direction along the longitudinal axis A of the operating part 22 depending on the operation of the erection operating lever 20 (refer to FIG. 9).

Figure 29:
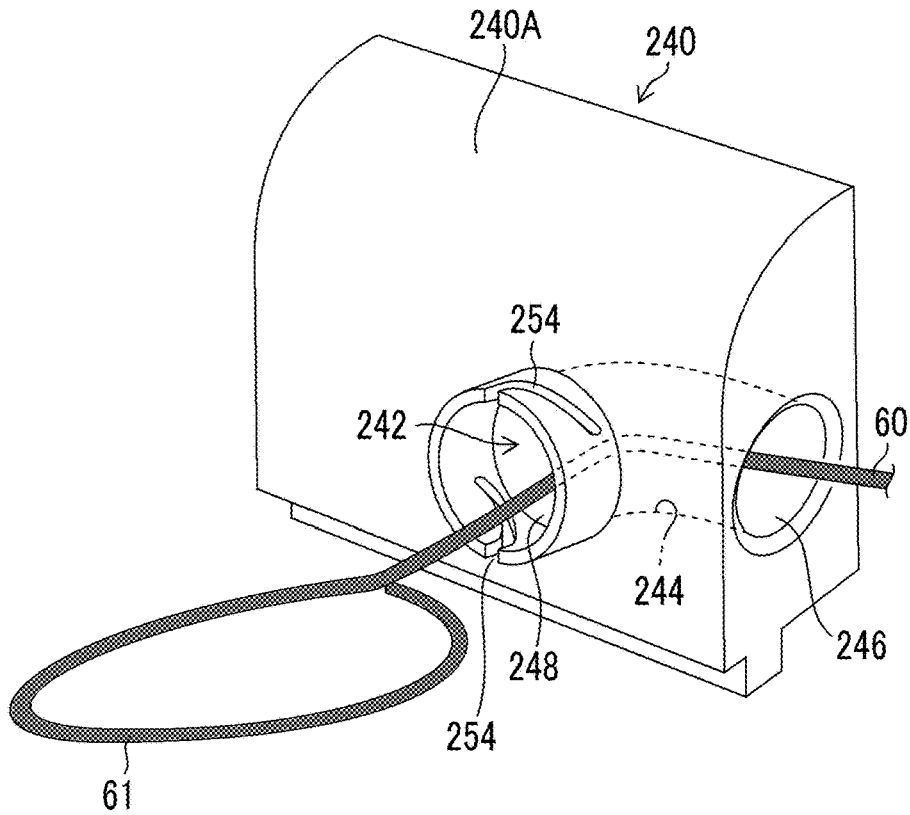
FIG. 29 is an enlarged perspective view illustrating the structure of the slider.

As illustrated in FIG. 26, the engaged part 242 is formed on a front surface 240A of the slider 240. The engaged part 242 is recessed in the front surface 240A of the slider 240 such that an opening part 242A of the engaged part 242 faces the lateral side (a direction of arrow P) orthogonal to the movement direction of the slider 240. Additionally, as illustrated in FIG. 29, a wire insertion passage 244 is formed in the slider 240. FIG. 29 is an enlarged perspective view illustrating the structure of the slider 240.

The wire insertion passage 244 is a passage that allows an opening part 246 disposed at a position facing the opening part 94 (refer to FIG. 26) of the wire channel 62 and an opening part 248 formed in the engaged part 242 to communicate with each other, and is formed inside the slider 240. In a case where the distal end of the wire 60 is coupled to the elevator 30 (refer to FIG. 3), the wire 60 is inserted into the wire insertion passage 244 from the opening part 248 and is inserted into the opening part 94 (refer to FIG. 19) from the opening part 246.

The engaging member 250, which is engageable with the engaged part 242, is formed as a hemisphere as illustrated in FIG. 26. The engaging member 250 is pushed into the engaged part 242 in a direction of arrow Q of FIG. 26 from the lateral side orthogonal to the movement direction of the slider 240. As a result, the engaging member 250 is engaged with the engaged part 242 with elasticity.

Additionally, the connection structure of the fourth embodiment comprises a locking mechanism. This locking mechanism is switchable between a locked position (refer to FIG. 28) where release of an engaged state between the engaging member 250 and the engaged part 242 is prevented and an unlocked position (refer to FIG. 27) where the release of the engaged state between the engaging member 250 and the engaged part 242 is allowed.

The locking mechanism is configured to comprise a pair of cam pins 252 that is cam engaging parts provided on an outer peripheral surface of the engaging member 250, and a pair of cam grooves 254 that is provided in the engaged part 242 and engages with the cam pin 252. The cam groove 254 is spirally formed toward the direction of arrow Q. As the cam pin 252 is pushed into the direction of arrow Q while being guided by the cam groove 254, the engaging member 250 and the engaged part 242 are engaged with each other and reach the locked position (refer to FIG. 28).

Next, the connection work of connecting the proximal end side of the wire 60 to the slider 240 by the connection structure of the fourth embodiment will be described.

First, the distal end of the wire 60 is inserted through the wire channel 62 via the wire insertion passage 244, the opening part 246, and the opening part 94 (refer to FIG. 26) from the opening part 248 (refer to FIG. 29) of the slider 240. Then, the distal end of the wire 60 is coupled to the elevator 30 (refer to FIG. 3).

Next, the erection operating lever 20 (refer to FIG. 9) is operated to locate the slider 240 at the erected position of FIG. 26.

Thereafter, a finger is hooked on the loop part 61 of the wire 60 to pull the wire 60 in the pulling direction and loosen the wire 60. In this state, the engaging member 250 is pushed into the engaged part 242 in the direction of arrow Q from the lateral side orthogonal to the movement direction of the slider 240. By this pushing work, the engaging member 250 is engaged with the engaged part 202 with elasticity. As illustrated in FIG. 27, in a case where the engaging member 250 is engaged with the engaged part 242, the proximal end side of the wire 60 protruding from the opening part 248 to the outside is sandwiched between the engaged part 242 and the engaging member 250. As a result, the proximal end side of the wire 60 is fixed to the slider 240.

Next, in a case where the engaging member 250 in the state of the unlocked position of FIG. 27 is rotated along the cam groove 254, as illustrated in FIG. 28, the cam pin 252 of the engaging member 250 is engaged with the cam groove 254 of the engaged part 242 and reaches the locked position. As a result, the slip-out of the engaging member 250 in the direction of arrow P with respect to the engaged part 242 can be prevented. Thus, the above connection work is completed.

In this way, according to the connection structure of the fourth embodiment, the connection work of connecting the proximal end side of the wire 60 to the slider 240 can be performed simply by the work of pushing the engaging member 250 into the engaged part 242 and the work of engaging the cam pin 252 with the cam groove 254. As a result, according to the connection structure of the fourth embodiment, the proximal end side of the wire 60 can be easily connected to the slider 240.

On the other hand, in a case where the proximal end side of the wire 60 is detached from the slider 240, first, the engaging member 250 in the state of the locked position of FIG. 28 is rotated in the opposite direction along the cam groove 254. As a result, the engaging member 250 can be located at the unlocked position illustrated in FIG. 27. Next, the engaging member 250 is pulled out from the engaged part 242 in the direction (the direction of arrow P: refer to FIG. 26) opposite to the pushing direction (the direction of arrow Q: refer to FIG. 26) of the engaging member 250 with respect to the engaged part 242. The detachment work is completed simply by this work. Therefore, according to the connection structure of the fourth embodiment, the proximal end side of the wire 60 can be easily detached from the slider 240.

As described above, according to the connection structure of the fourth embodiment, the connection work of connecting the proximal end side of the wire 60 to the slider 240 can be performed simply by the work of pushing the engaging member 250 into the engaged part 242 and the work of engaging the cam pin 252 with the cam groove 254. Additionally, the detachment work of detaching the proximal end side of the wire 60 from the slider 240 can be performed simply by the work of removing the cam pin 252 from the cam groove 254 and the work of pulling the engaging member 250 from the engaged part 242. Additionally, according to the connection structure of the fourth embodiment, the proximal end side of the wire 60 can also be connected to the slider 240 simply by the work of pushing the engaging member 250 into the engaged part 242. Additionally, according to the connection structure of the fourth embodiment, the proximal end side of the wire 60 can also be detached from the slider 240 simply by the work of pulling the engaging member 250 from the engaged part 242.

Hence, according to the connection structure of the fourth embodiment, the attachment and detachment work of the proximal end side of the wire 60 with respect to the slider 240 can be easily performed similarly to the connection structures of the above-described respective embodiments.

In addition, according to the connection structure of the fourth embodiment, the cam pin 252 is provided in the engaging member 250, and the cam groove 254 is provided in the engaged part 242. However, the cam groove 254 may be provided in the engaging member 250, and the cam pin 252 may be provided in the engaged part 242.

Additionally, in the connection structure of the fourth embodiment, the following work can be easily performed using a jig. The above work is the work of pushing the engaging member 250 into the engaged part 242, the locking work of rotating the engaging member 250 from the unlocked position to the locked position, the unlocking work of rotating the engaging member 250 from the locked position to the unlocked position, and the work of pulling the engaging member 250 from the engaged part 242.

Figure 30:
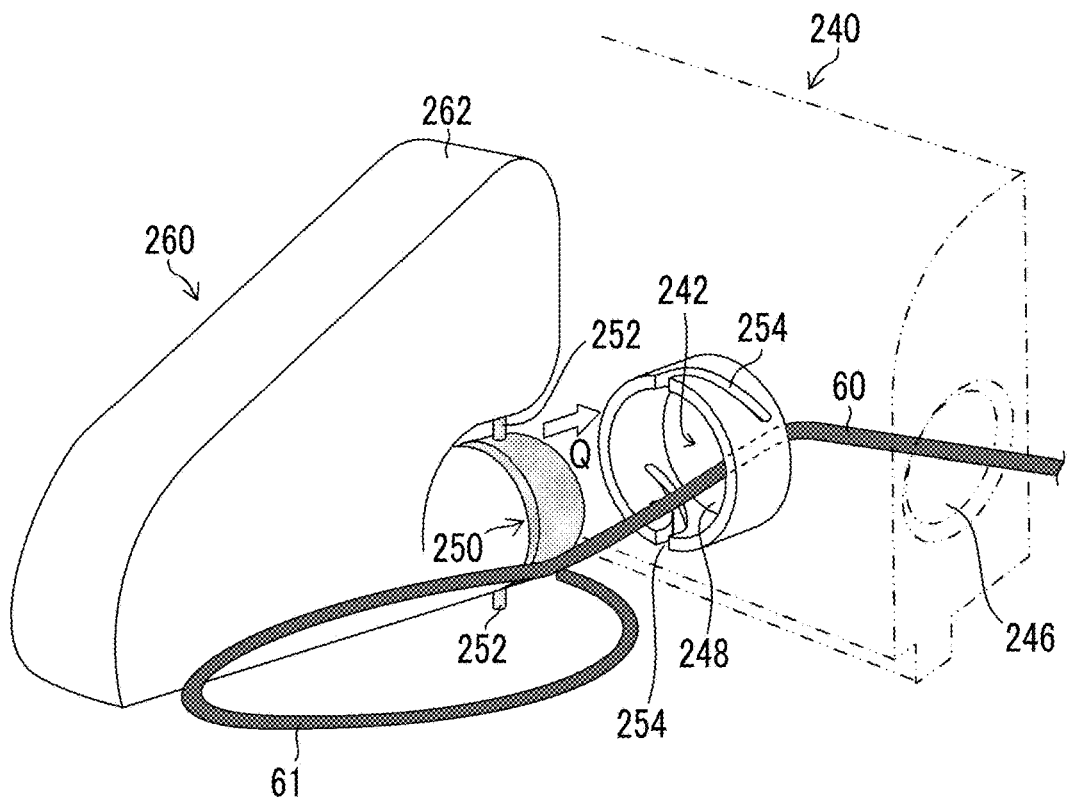
FIG. 30 is an explanatory view of the work in which the engaging member is pushed into the engaged part using the jig.

FIG. 30 is an explanatory view of the work of pushing the engaging member 250 into the engaged part 242 using a jig 260. Additionally, FIG. 31 is an enlarged perspective view of main parts illustrating an engagement relationship between the jig 260 and the engaging member 250.

Figure 31:
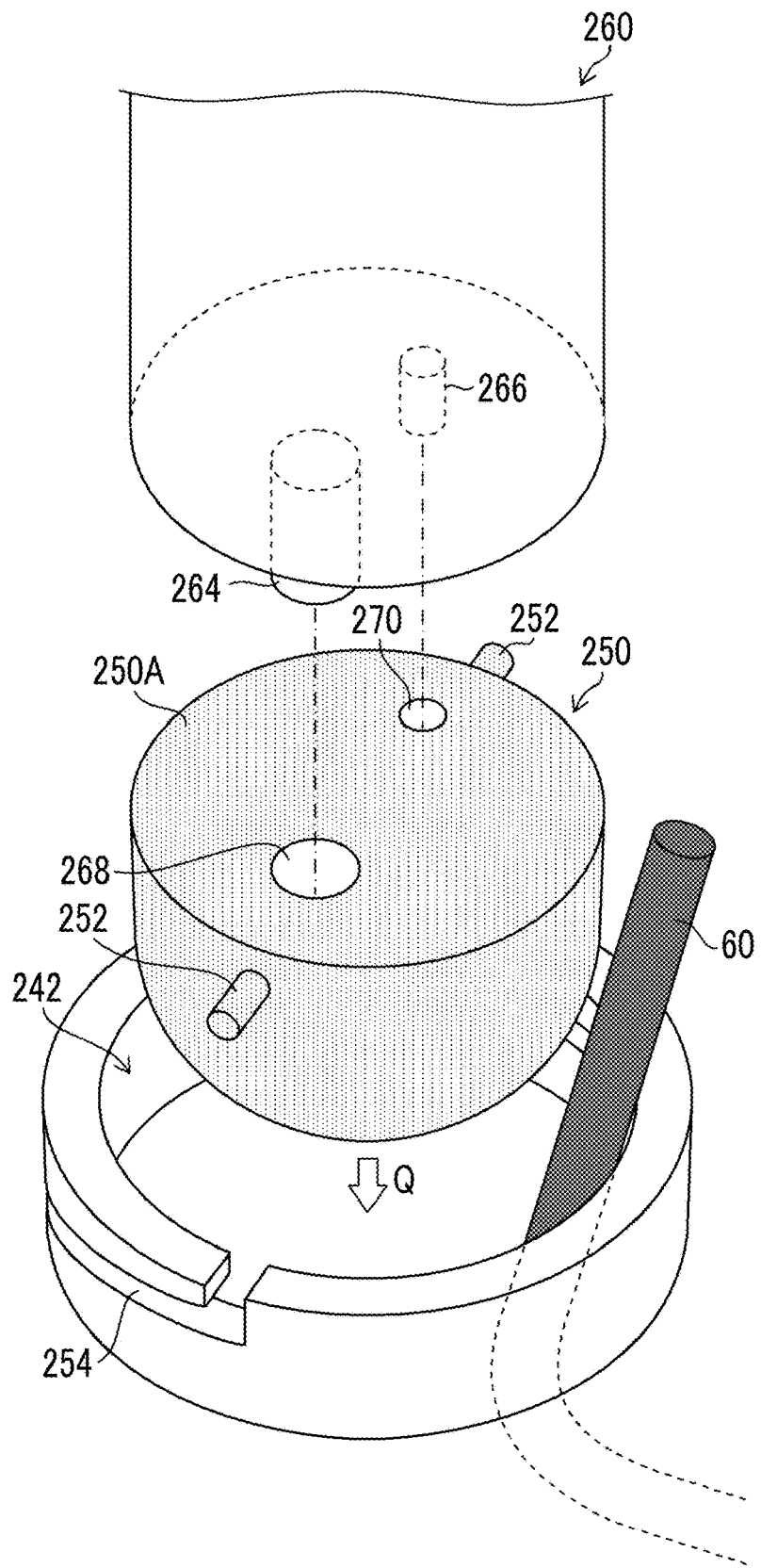
FIG. 31 is an enlarged perspective view of main parts illustrating an engagement relationship between the jig and the engaging member.

As illustrated in FIGS. 30 and 31, the jig 260 comprises a knob 262, and two pins 264 and 266 provided to protrude from an end part of the knob 262. Additionally, a flat end surface 250A of the engaging member 250 is provided with a hole 268 into which the pin 264 is fitted, and a hole 270 into which the pin 266 is fitted. The engaging member 250 is attachably and detachably attached to the jig 260 (refer to FIG. 30) as the pin 264 is fitted into the hole 268 and the pin 266 is fitted into the hole 270.

Next, the work of pushing the engaging member 250 into the engaged part 242 is performed. In this work, first, a finger is hooked on the loop part 61 of the wire 60 to pull the wire 60 in the pulling direction and loosen the wire 60. In this state, the engaging member 250 is pushed into the engaged part 242 in the direction of arrow Q in the state of FIG. 30 where the engaging member is attached to the jig 260.

Figures 32, 33:
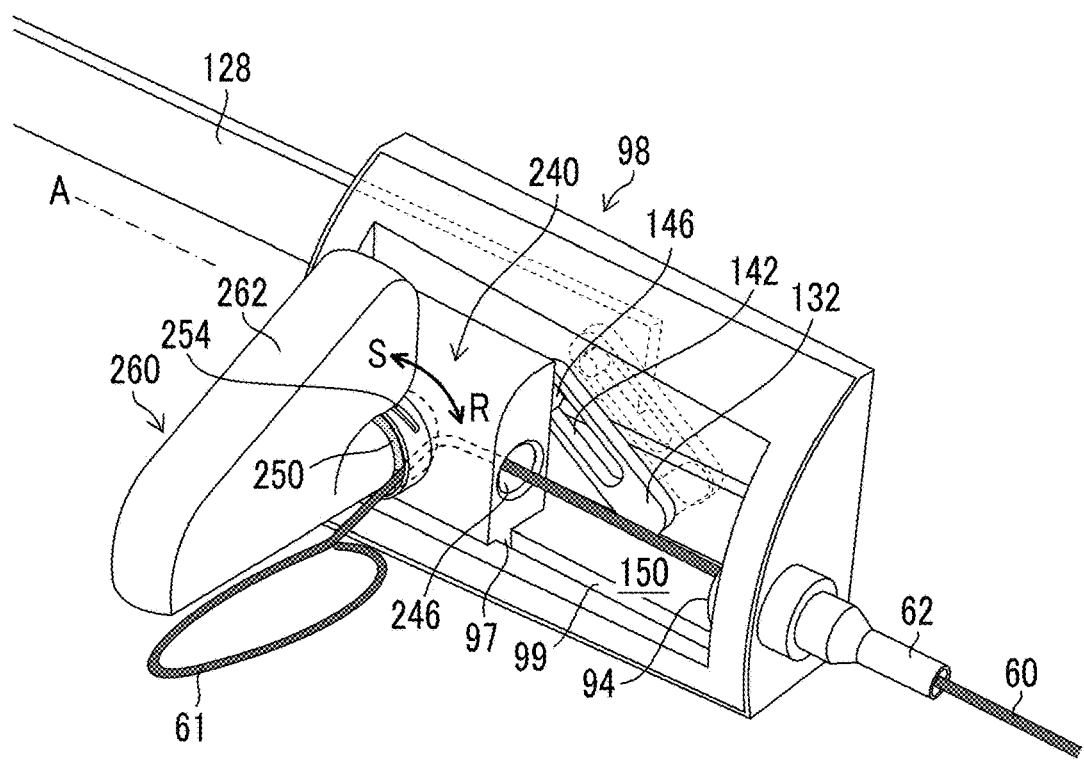
FIG. 32 is an explanatory view illustrating a state where the engaging member is pushed into the engaged part using the jig.
FIG. 33 is an enlarged perspective view of main parts of the engaging member pushed into the engaged part.

FIG. 32 is an explanatory view illustrating a state where the engaging member 250 is pushed into the engaged part 242 using the jig 260. FIG. 33 is an enlarged perspective view of main parts illustrating a state where the engaging member 250 is pushed into the engaged part 242. The position of the engaging member 250 with respect to the engaged part 242 in FIGS. 32 and 33 is the unlocked position.

Figure 34:
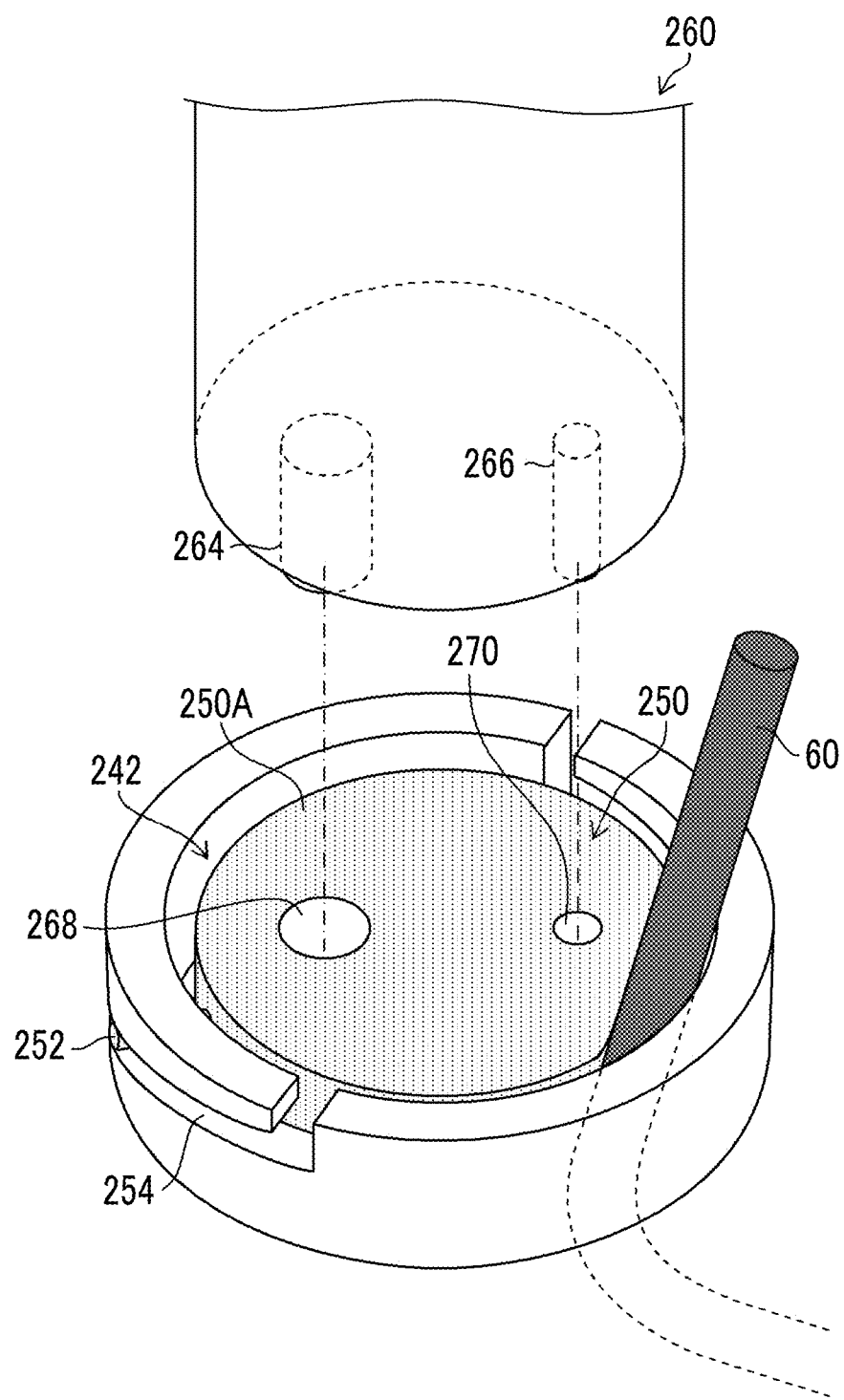
FIG. 34 is an enlarged perspective view of main parts in which a cam pin is engaged with a cam groove by the jig.

Next, the locking work is performed. In this work, the jig 260 is rotated in a direction of arrow R of FIG. 32. As a result, the cam pin 252 is pushed along the cam groove 254, and the cam pin 252 is engaged with the cam groove 254 and reaches the locked position (refer to FIG. 34). FIG. 34 is an enlarged perspective view of main parts in which the cam pin 252 is engaged with the cam groove 254 by the rotation of the jig 260.

In a case where the engaging member 250 is detached from the engaged part 242, first, the unlocking work is performed. In this work, the jig 260 is rotated in a direction of arrow S of FIG. 32. As a result, the engagement between the cam pin 252 and the cam groove 254 is released and the unlocked position (refer to FIG. 33).

Next, the pulling-out work of the engaging member 250 is performed. In this work, the jig 260 is pulled out in a pulling-out direction (the direction of arrow P: refer to FIG. 26). As a result, the engaging member 250 can be easily pulled out from the engaged part 242.

In a case where the endoscope 10 is used, the jig 260 illustrated in FIGS. 30 to 34 may be detached from the engaging member 250 or may be mounted on the engaging member 250 as it is.

In the above embodiment, the duodenoscope has been exemplified and described as the endoscope 10. However, as long as an endoscope comprising an elevator for adjusting the delivery direction of a treatment tool at a distal end part of an insertion part is provided, the invention can be applied to various endoscopes, such as an ultrasonic endoscope.

EXPLANATION OF REFERENCES

10: endoscope
12: endoscope system
14: processor device
16: light source device
18: display
20: erection operating lever
22: operating part
23: opening part
24: insertion part
26: distal end part
28: distal end member
28A: peripheral surface
30: elevator
30A: guide surface
30B: proximal part
32: operating part body
34: gripping part
38: folding-preventing tube
38A: proximal end part
42: treatment tool introduction port
46: universal cord
48: electric connector
50: light source connector
52: bending part
54: flexible part
56: treatment tool
56A: distal end part
58: treatment tool channel
60: wire
61: loop part
62: wire channel
64: angle knob
66: air/water supply button
68: suction button
70: air/water supply nozzle
72: treatment tool delivery port
74: delivery port
76: cap
76A: opening window
78: partition wall
78A: bearing part
80: partition wall
80A: bearing part
82: elevator housing chamber
84: rotational movement shaft
86: rotational movement shaft
88: optical system housing chamber
90: illumination window
92: observation window
94: opening part
96: slider
97: protruding strip
98: base member
99: recessed strip
98A: body part
98B: wall part
98C: proximal end wall
98D: distal end wall
100: engaging member
102: housing groove
104: opening
106: engagement guide part 108: engagement guide path
110: deformation generating part
112: groove
114: groove
116: separation guide surface
120: erection operating mechanism
124: arm
126: drive shaft
128: drive arm
130: first lever
130A: one end part
130B: other end part
132: second lever
132A: one end part
132B: other end part
134: cam pin
136: cam groove
138: rotating shaft
140: O-ring
142: cam groove
144: rotating shaft
146: cam pin
150: slider housing space
152: engaged part
152A: opening part
154: engaging member
156: engagement receiving part
158: positioning receiving part
160: engaging body part
162: positioning part
163: proximal-end-side end surface
164: guide surface
170: slider
170A: front surface
172: engaged part
172A: opening part
173: guide surface
174: wire insertion passage
176: opening part
178: opening part
180: engaging member
180A: center
182: sandwiching part
182A: bottom surface
190: jig
192: acute part
194: projection
196: recess
200: slider
200A: front surface
202: engaged part
202A: opening part
204: wire insertion passage
206: opening part
208: opening part
210: engaging member
212: rotating shaft
214: knob
216: locking operating member
218: locking member
220: bracket
222: sandwiching part
224: slit
226: slit
228: slit
230: groove
232: opening part
234: locking recess
236: escape part
240: slider
240A: front surface
242: engaged part
242A: opening part
244: wire insertion passage
246: opening part
248: opening part
250: engaging member
250A: end surface
252: cam pin
254: cam groove
260: jig
262: knob
264: pin
266: pin
268: hole
270: hole
300: branched tube
302: distal end tube
304: pipe line
306: pipe line

What is claimed is:

1. An endoscope comprising:
an operating part that is provided with an operating member;
an insertion part that is provided on a distal end side of the operating part and is inserted into a subject;
an elevator that is provided at a distal end part of the insertion part;
an erection operating wire that is disposed to be inserted through a wire insertion passage formed from the operating part to the insertion part so as to be movable forward and backward and is attachably and detachably coupled to the elevator on a distal end side thereof;
a base member that is provided in the operating part and forms a slider housing space that is independent of an internal space of the operating part;
an opening part that is provided at a proximal end of the wire insertion passage and delivers a proximal end side of the erection operating wire to the slider housing space;
a slider that is disposed in the slider housing space and is movable forward and backward in a longitudinal direction of the operating part depending on an operation of the operating member;
an engaged part that is provided in the slider and is recessed or protrudes toward a lateral side orthogonal to a movement direction of the slider;
an engaging member, comprising a column, that is provided at a proximal end of the erection operating wire and is pushed into and engageable with the engaged part from the lateral side;
a first lever, having a first linear cam groove,
a second lever, having a second linear cam groove, the second lever is coupled to the first lever, the second lever is configured to convert rotary motion of the first lever into a linear motion and transmit the linear motion to the slider,
wherein the slider housing space is exposable to outside of the operating part,
wherein the slider includes a cam pin that protrudes from the slider,
wherein the cam pin is slidably disposed in the second linear cam groove of the second lever.

2. The endoscope according to claim 1,
wherein the engaged part has an engagement receiving part that extends linearly in the movement direction of the slider, and a positioning receiving part that is provided at the engagement receiving part and positions the engaging member in the engaged part, and
wherein the engaging member has an engaging body part that engages with the engagement receiving part, and a positioning part, comprising a head part that is formed to have a larger diameter than the column, that engages with the positioning receiving part.

3. The endoscope according to claim 2,
wherein the column constitutes the engaging body part, and the head part constitutes the positioning part.

4. The endoscope according to claim 2,
wherein the slider has a guide surface that guides the positioning part to the positioning receiving part.

5. The endoscope according to claim 1,
wherein the slider housing space is exposable to outside of the operating part.

6. The endoscope according to claim 1,
wherein the engaging member engages with the engaged part with elasticity.

7. The endoscope according to claim 1, further comprising
a cap configured to block the slider housing space.

8. An endoscope comprising:
an operating part that is provided with an operating member;
an insertion part that is provided on a distal end side of the operating part and is inserted into a subject;
an elevator that is provided at a distal end part of the insertion part;
an erection operating wire that is disposed to be inserted through a wire insertion passage formed from the operating part to the insertion part so as to be movable forward and backward and is attachably and detachably coupled to the elevator on a distal end side thereof;
a base member that is provided in the operating part and forms a slider housing space that is independent of an internal space of the operating part;
an opening part that is provided at a proximal end of the wire insertion passage and delivers a proximal end side of the erection operating wire to the slider housing space;
a slider that is disposed in the slider housing space and is movable forward and backward in a longitudinal direction of the operating part depending on an operation of the operating member;
an engaged part that is provided in the slider and is recessed or protrudes toward a lateral side orthogonal to a movement direction of the slider;
an engaging member, comprising a column, that is provided at a proximal end of the erection operating wire and is pushed into and engageable with the engaged part from the lateral side;
a first lever, having a first linear cam groove,
a second lever, having a second linear cam groove, the second lever is coupled to the first lever, the second lever is configured to convert rotary motion of the first lever into a linear motion and transmit the linear motion to the slider,
wherein the engaging member engages with the engaged part with elasticity,
wherein the slider includes a cam pin that protrudes from the slider,
wherein the cam pin is slidably disposed in the second linear cam groove of the second lever.

* * * * *